US009144508B2

(12) United States Patent
Hebert et al.

(10) Patent No.: US 9,144,508 B2
(45) Date of Patent: Sep. 29, 2015

(54) RADIALLY EXPANDABLE STENT

(75) Inventors: Stephen Hebert, San Francisco, CA (US); Marc-Alan Levine, Pottstown, PA (US); Aleksandr Leynov, Walnut Creek, CA (US)

(73) Assignee: Back Bay Medical Inc., Costa Mesa, CA (US)

(*) Notice: Subject to any disclaimer, the term of this patent is extended or adjusted under 35 U.S.C. 154(b) by 1356 days.

(21) Appl. No.: 11/948,928

(22) Filed: Nov. 30, 2007

(65) Prior Publication Data

US 2009/0024205 A1 Jan. 22, 2009

Related U.S. Application Data

(60) Provisional application No. 60/961,181, filed on Jul. 19, 2007.

(51) Int. Cl.
*A61F 2/06* (2013.01)
*A61F 2/915* (2013.01)
*A61F 2/91* (2013.01)

(52) U.S. Cl.
CPC . *A61F 2/915* (2013.01); *A61F 2/91* (2013.01); *A61F 2002/9155* (2013.01); *A61F 2002/91533* (2013.01); *A61F 2002/91558* (2013.01); *A61F 2002/91583* (2013.01); *A61F 2230/0054* (2013.01)

(58) Field of Classification Search
CPC .......................................................... A61F 2/06
USPC ............. 623/1.42, 1.15, 1.18, 1.46, 1.34, 1.1, 623/1.2
See application file for complete search history.

(56) References Cited

U.S. PATENT DOCUMENTS

| 3,485,234 | A | 12/1969 | Stevens |
|---|---|---|---|
| 3,517,128 | A | 6/1970 | Hines |
| 4,586,923 | A | 5/1986 | Gould |
| 4,665,918 | A | 5/1987 | Garza |
| 4,768,507 | A | 9/1988 | Fischell |
| 4,787,884 | A | 11/1988 | Goldberg |
| 4,969,890 | A | 11/1990 | Sugita |
| 4,990,151 | A | 2/1991 | Wallsten |
| 4,994,071 | A | 2/1991 | MacGregor |
| 5,034,001 | A | 7/1991 | Garrison |
| 5,092,877 | A | 3/1992 | Pinchuk |
| 5,098,440 | A | 3/1992 | Hillstead |
| 5,147,370 | A | 9/1992 | McNamara |

(Continued)

FOREIGN PATENT DOCUMENTS

| DE | 19937638 A1 | 5/2001 |
|---|---|---|
| EP | 0221570 A2 | 5/1987 |

(Continued)

OTHER PUBLICATIONS

Supplementary European Search Report (Nov. 17, 2006).

(Continued)

*Primary Examiner* — Thomas J Sweet
*Assistant Examiner* — Matthew Schall
(74) *Attorney, Agent, or Firm* — Peter B. Scull; Hamilton, DeSanctis & Cha, LLP

(57) ABSTRACT

A highly compressible stent is described. The stent includes a plurality of circumferentially offset and interconnected undulating rings having intermediate struts disposed between at least some of the undulating ring struts.

29 Claims, 18 Drawing Sheets

(56) References Cited

U.S. PATENT DOCUMENTS

| | | |
|---|---|---|
| 5,342,387 A | 8/1994 | Summers |
| 5,368,592 A | 11/1994 | Stern |
| 5,391,146 A | 2/1995 | That |
| 5,453,090 A | 9/1995 | Martinez |
| 5,458,615 A | 10/1995 | Klemm |
| 5,464,408 A | 11/1995 | Duc |
| 5,484,444 A | 1/1996 | Braunschweiler |
| 5,498,227 A | 3/1996 | Mawad |
| 5,534,007 A | 7/1996 | St. Germain |
| 5,571,086 A | 11/1996 | Kaplan |
| 5,571,135 A | 11/1996 | Fraser |
| 5,607,466 A | 3/1997 | Imbert |
| 5,669,924 A | 9/1997 | Shaknovich |
| 5,683,451 A | 11/1997 | Lenker |
| 5,702,418 A | 12/1997 | Ravenscroft |
| 5,735,859 A | 4/1998 | Fischell |
| 5,749,825 A | 5/1998 | Fischell |
| 5,755,708 A | 5/1998 | Segal |
| 5,772,669 A | 6/1998 | Vrba |
| 5,776,141 A | 7/1998 | Klein |
| 5,782,855 A | 7/1998 | Lau |
| 5,788,707 A | 8/1998 | Del Toro |
| 5,797,952 A | 8/1998 | Klein |
| 5,807,398 A | 9/1998 | Shaknovich |
| 5,810,872 A | 9/1998 | Kanesaka et al. |
| 5,824,041 A | 10/1998 | Lenker |
| 5,824,055 A | 10/1998 | Spiridigliozzi |
| 5,827,321 A | 10/1998 | Roubin et al. |
| 5,843,090 A | 12/1998 | Schuetz |
| 5,855,600 A | 1/1999 | Alt |
| 5,906,640 A | 5/1999 | Penn |
| 5,910,144 A | 6/1999 | Hayashi |
| 5,957,227 A | 9/1999 | Besson et al. |
| 5,957,929 A | 9/1999 | Brenneman |
| 5,961,548 A | 10/1999 | Shmulewitz |
| 5,972,018 A | 10/1999 | Israel et al. |
| 5,980,533 A | 11/1999 | Holman |
| 5,989,280 A | 11/1999 | Euteneuer |
| 6,042,588 A | 3/2000 | Munsinger |
| 6,056,775 A | 5/2000 | Borghi |
| 6,059,822 A | 5/2000 | Kanesaka et al. |
| 6,071,286 A | 6/2000 | Mawad |
| 6,129,755 A | 10/2000 | Mathis et al. |
| 6,146,415 A | 11/2000 | Fitz |
| 6,156,063 A | 12/2000 | Douglas |
| 6,162,243 A | 12/2000 | Gray et al. |
| 6,168,579 B1 | 1/2001 | Tsugita |
| 6,168,617 B1 | 1/2001 | Blaeser |
| 6,171,328 B1 | 1/2001 | Addis |
| 6,179,859 B1 | 1/2001 | Bates |
| 6,183,481 B1 | 2/2001 | Lee |
| 6,187,015 B1 | 2/2001 | Brenneman |
| 6,187,016 B1 | 2/2001 | Hedges |
| 6,190,403 B1 | 2/2001 | Fischell et al. |
| 6,206,911 B1 | 3/2001 | Milo |
| 6,210,429 B1 | 4/2001 | Vardi |
| 6,217,585 B1 | 4/2001 | Houser |
| 6,238,409 B1 | 5/2001 | Hojeibane |
| 6,241,758 B1 | 6/2001 | Cox |
| 6,245,045 B1 | 6/2001 | Stratienko |
| 6,254,609 B1 | 7/2001 | Vrba |
| 6,254,628 B1 | 7/2001 | Wallace |
| 6,261,319 B1 | 7/2001 | Kveen et al. |
| 6,264,671 B1 | 7/2001 | Stack |
| 6,264,682 B1 | 7/2001 | Wilson |
| 6,270,521 B1 | 8/2001 | Fischell |
| 6,280,465 B1 | 8/2001 | Cryer |
| 6,296,622 B1 | 10/2001 | Kurz |
| 6,309,414 B1 | 10/2001 | Rolando et al. |
| 6,322,586 B1 | 11/2001 | Monroe |
| 6,350,278 B1 | 2/2002 | Lenker |
| 6,368,344 B1 | 4/2002 | Fitz |
| 6,390,993 B1 | 5/2002 | Cornish |
| 6,391,044 B1 | 5/2002 | Yadav |
| 6,391,050 B1 | 5/2002 | Broome |
| 6,391,051 B2 | 5/2002 | Sullivan, III |
| 6,398,805 B1 | 6/2002 | Alt |
| 6,409,750 B1 | 6/2002 | Hyodoh |
| 6,425,898 B1 | 7/2002 | Wilson |
| 6,461,381 B2 | 10/2002 | Israel et al. |
| 6,464,720 B2 | 10/2002 | Boatman et al. |
| 6,468,298 B1 | 10/2002 | Pelton |
| 6,478,816 B1 * | 11/2002 | Kveen et al. ................. 623/1.15 |
| 6,508,825 B1 | 1/2003 | Selmon |
| 6,514,280 B1 | 2/2003 | Gilson |
| 6,514,281 B1 | 2/2003 | Blaeser |
| 6,520,988 B1 | 2/2003 | Colombo |
| 6,582,460 B1 | 6/2003 | Cryer |
| 6,592,549 B2 | 7/2003 | Gerdts |
| 6,602,282 B1 * | 8/2003 | Yan ............................. 623/1.15 |
| 6,607,551 B1 | 8/2003 | Sullivan |
| 6,616,690 B2 | 9/2003 | Rolando et al. |
| 6,626,934 B2 | 9/2003 | Blaeser |
| 6,673,025 B1 | 1/2004 | Richardson |
| 6,679,909 B2 | 1/2004 | McIntosh |
| 6,695,862 B2 | 2/2004 | Cox |
| 6,699,278 B2 | 3/2004 | Fischell et al. |
| 6,706,061 B1 | 3/2004 | Fischell et al. |
| 6,743,219 B1 | 6/2004 | Dwyer |
| 6,755,846 B1 | 6/2004 | Yadav |
| 6,764,507 B2 | 7/2004 | Shanley et al. |
| 6,796,997 B1 | 9/2004 | Penn et al. |
| 6,802,846 B2 | 10/2004 | Hauschild |
| 6,833,003 B2 | 12/2004 | Jones |
| 6,840,950 B2 | 1/2005 | Stanford |
| 6,860,898 B2 | 3/2005 | Stack |
| 6,890,349 B2 | 5/2005 | McGuckin, Jr. |
| 6,908,477 B2 | 6/2005 | McGuckin, Jr. |
| 6,926,732 B2 | 8/2005 | Derus |
| 6,932,836 B2 | 8/2005 | Amin |
| 6,936,065 B2 | 8/2005 | Khan |
| 6,939,368 B2 | 9/2005 | Simso |
| 6,945,989 B1 | 9/2005 | Betelia |
| 6,949,120 B2 | 9/2005 | Kveen et al. |
| 6,955,685 B2 | 10/2005 | Escamilla |
| 6,955,686 B2 | 10/2005 | Majercak et al. |
| 6,960,227 B2 | 11/2005 | Jones |
| 6,989,024 B2 | 1/2006 | Hebert |
| 7,001,422 B2 | 2/2006 | Escamilla |
| 7,004,964 B2 | 2/2006 | Thompson |
| 7,011,673 B2 | 3/2006 | Fischell |
| 7,029,493 B2 | 4/2006 | Majercak et al. |
| 7,037,330 B1 | 5/2006 | Rivelli, Jr. |
| 7,060,088 B1 | 6/2006 | Fischell et al. |
| 7,063,719 B2 | 6/2006 | Jansen |
| 7,182,779 B2 | 2/2007 | Acosta |
| 7,220,275 B2 | 5/2007 | Davidson et al. |
| 2001/0027323 A1 | 10/2001 | Sullivan, III |
| 2001/0027339 A1 * | 10/2001 | Boatman et al. ............. 623/1.15 |
| 2001/0037126 A1 | 11/2001 | Stack |
| 2002/0049487 A1 | 4/2002 | Lootz |
| 2002/0151964 A1 | 10/2002 | Smith et al. |
| 2002/0161427 A1 | 10/2002 | Rabkin |
| 2003/0004567 A1 | 1/2003 | Boyle et al. |
| 2003/0114918 A1 * | 6/2003 | Garrison et al. ............. 623/1.13 |
| 2004/0010265 A1 | 1/2004 | Karpiel |
| 2004/0059407 A1 | 3/2004 | Escamilla |
| 2004/0102834 A1 | 5/2004 | Nakano et al. |
| 2004/0186551 A1 * | 9/2004 | Kao et al. .................... 623/1.15 |
| 2004/0193178 A1 | 9/2004 | Nikolchev |
| 2004/0193179 A1 | 9/2004 | Nikolchev |
| 2004/0220585 A1 | 11/2004 | Nikolchev |
| 2004/0260381 A1 | 12/2004 | Marco |
| 2004/0260385 A1 | 12/2004 | Jones |
| 2005/0209670 A1 | 9/2005 | George |
| 2005/0209671 A1 | 9/2005 | Ton |
| 2005/0209672 A1 | 9/2005 | George |
| 2005/0209675 A1 | 9/2005 | Ton |
| 2005/0246008 A1 | 11/2005 | Hogendijk |
| 2006/0085057 A1 | 4/2006 | George |
| 2006/0136037 A1 | 6/2006 | DeBeer |
| 2006/0206200 A1 | 9/2006 | Garcia |
| 2006/0206201 A1 | 9/2006 | Garcia |
| 2006/0271149 A1 | 11/2006 | Berez |

(56) References Cited

U.S. PATENT DOCUMENTS

| | | |
|---|---|---|
| 2006/0271153 A1 | 11/2006 | Garcia |
| 2007/0027522 A1 | 2/2007 | Chang |
| 2007/0043419 A1 | 2/2007 | Nikolchev |
| 2007/0055339 A1 | 3/2007 | George |
| 2007/0073379 A1 | 3/2007 | Chang |
| 2007/0173925 A1 | 7/2007 | Fliedner |

FOREIGN PATENT DOCUMENTS

| | | |
|---|---|---|
| EP | 0997116 | 5/2000 |
| WO | WO9639998 | 12/1996 |
| WO | WO9707756 | 3/1997 |
| WO | WO9745073 | 12/1997 |
| WO | WO9849983 | 11/1998 |
| WO | WO9934749 | 7/1999 |
| WO | WO9936002 | 7/1999 |
| WO | WO9955253 A6 | 11/1999 |
| WO | WO0000190 | 2/2000 |
| WO | WO0072780 | 12/2000 |
| WO | WO0149214 | 7/2001 |
| WO | WO03041610 | 5/2003 |

OTHER PUBLICATIONS

Cordis Neurovascular, Inc 2002 US ref: 152-7369-2; Johnson & Johnson Medical NV/SA EU ref: 2E-800-0475-4; "Rapidtransit Microcatheter 18 System through tortuous vasculature".

Randall T. Higashida, et al., "Initial Clinical Experience with a New Self-Expanding Nitinol Stent for the Treatment of Intracranial Cerebral Aneurysms: The Cordis Enterprise Stent", pp. 1751-1756.

Alexandre C. Abizaid, et al., "The CariodMind coronary stent delivery system", Europe Edition 2007, pp. 154-157.

USPTO, Transmittal of International Search Report and the Written Opinion of the International Searching Authority for International Application No. PCT/US2008/070382, Oct. 22, 2008.

International Bureau of WIPO, Notification Concerning Transmittal of International Preliminary Report on Patentability for International Application No. PCT/US2008/070382, Jan. 28, 2010.

* cited by examiner

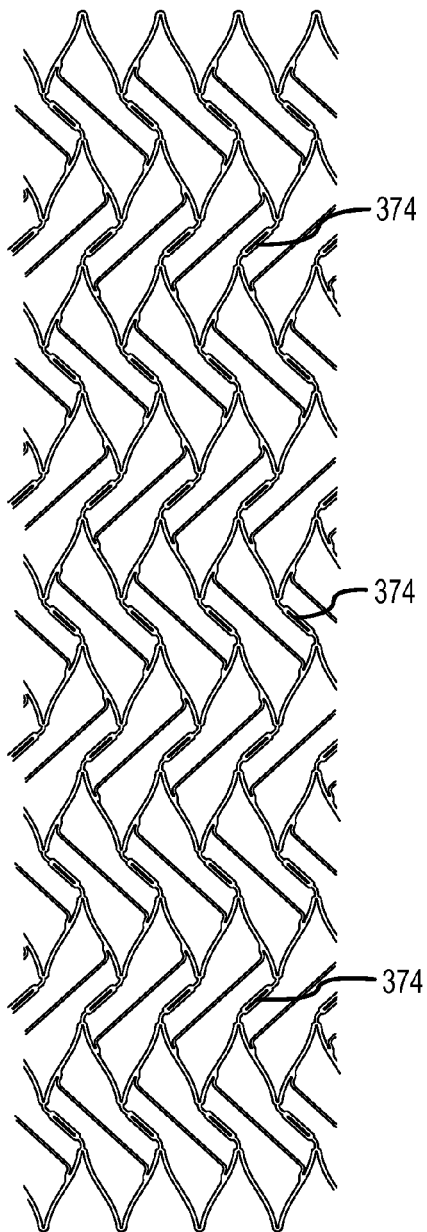
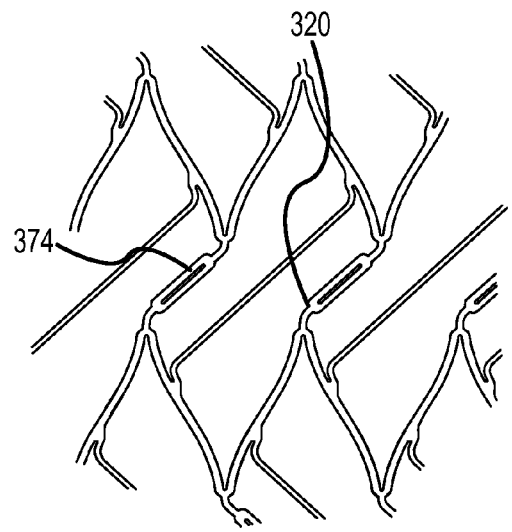
FIG.11B
FIG.11A

RADIALLY EXPANDABLE STENT

CROSS-REFERENCE TO RELATED APPLICATIONS

This application is related to and claims the benefit of the filing date of U.S. Provisional Patent Application Ser. No. 60/961,181, entitled EXPANDABLE STENT, filed Jul. 19, 2007.

BACKGROUND

1. Technical Field

This application relates to a stent, and more particularly to a stent that is compressible to small diameters to enable access to small vessels or ducts within the body.

2. Background of Related Art

Stents are well known in the medical arts for the treatment of vascular disease (e.g., vascular stenosis, aneurysms, etc.). Stents are prostheses which are generally tubular in form and which typically expand radially in a vessel or lumen to maintain its patency or for other therapeutic purposes. For deployment within the body's vascular system, some stents are mounted onto a balloon angioplasty catheter for deployment by balloon expansion at the site of a stenosis, an aneurysm, or other duct in need of treatment. Balloon-expandable stents are typically crimped onto the outer surface of a balloon located near the distal end of a catheter. The stent is expanded by inflation of the balloon and maintains its expanded configuration by virtue of being plastically deformed during the expansion process. Self-expanding stents, on the contrary, need little or no external force to move them from a compressed configuration to an expanded configuration. Self-expanding stents either self-expand due to exposure of environmental factors (e.g., body heat) and/or are radially constrained in a compressed/reduced diameter position on or within a delivery device and self-expand toward an original diameter when released from the delivery device so as to exert a radial force on the wall of the body lumen. Self-expanding stents are generally composed of shape memory alloys such as Nitinol, a nickel-titanium shape memory alloy, which can be formed and annealed, deformed at a low temperature, and recalled to its original shape with heating, such as when deployed at body temperature in the body.

Conventional percutaneous delivery of a stent to a treatment site generally includes introducing a guiding catheter having a preformed distal tip into the vascular system of a patient by way of, e.g., a conventional Seldinger technique, and advancing the guiding catheter within the vasculature until its distal tip is seated in the ostium of a desired artery. A guidewire is then advanced through an inner lumen of the guiding catheter until the distal end of the guidewire is placed across the treatment site. A stent delivery device carrying the stent is then advanced over the guidewire to properly position the stent across the treatment site. Once positioned, the stent is expanded for permanent placement at the treatment site.

Conventional stent delivery catheters share a common feature in that they are required to have a guidewire lumen to facilitate advancement of the catheter over the guidewire for placement of the stent. As a consequence, the guidewire lumen necessarily adds to the cross-sectional profile of the device and prohibits the use of these devices in the treatment of certain small diameter vessels and/or vessels located within tortuous regions of the vasculature (e.g., vessels located within the coronary and intracranial vasculature).

In commonly assigned U.S. Pat. No. 6,989,024, the entire contents of which are incorporated herein by reference, for all they teach or suggest, are disclosed methods and systems for delivering a vascular prosthesis (e.g., stent) that is mounted on a distal segment of an elongate wire or hyptoube. A major advantage of the wire-based delivery devices described in U.S. Pat. No. 6,989,024 is that the delivery devices obviate the need of a guidewire lumen in the delivery devices, and hence, facilitate the delivery of stents and other vascular prosthesis to small diameter vessels located within the tortuous anatomy of the body. For example, in one embodiment the vascular prosthesis is mounted on a reduced diameter portion of a wire, resulting in an overall reduced profile. Proximal and distal radiopaque marker bands, functioning as proximal and distal stops for the stent, are also described for certain embodiments. Reduced profile delivery systems are also disclosed in commonly assigned co-pending application Ser. Nos. 11/703,341 and 11/703,342, both filed on Feb. 7, 2007. The entire contents of these applications are incorporated herein by reference, for all they teach or suggest.

The present application provides a stent compressible to small diameters to provide access to small diameter vessels for use in neurovascular, cardiovascular as well as other clinical applications, and can be delivered via the wire-based devices disclosed in U.S. Pat. No. 6,989,024, in the Ser. Nos. 11/703,341 and 11/703,342 applications, or other devices, such as catheters.

SUMMARY OF THE INVENTION

A stent that is compressible to small diameters is described. In accordance with one embodiment a stent is provided comprising: at least first, second and third spaced-apart, radially expandable rings that are substantially aligned along a longitudinal axis, each ring comprising a plurality of first struts and a plurality of second struts, the first and second struts being connected to form an undulating pattern that has peak portions and valley portions, first curved connectors joining one or more of the valley portions of the first ring to one or more of the peak portions of the second ring, the valley portions and peak portions being circumferentially offset from one another, second curved connectors joining one or more of the valley portions of the second ring to one or more of the peak portions of the third ring, the valley portions and peak portions being circumferentially offset from one another, a first intermediate strut extending between a first strut of the first ring to a first strut of the second ring without intersecting any of the other first and second struts and first and second curved connectors and; a second intermediate strut extending between a second strut of the second ring to a second strut of the third ring without intersecting any of the other first and second struts and first and second curved connectors, the first and second intermediate struts being connected to locations on the first and second struts, respectively, such that no portions of the first and second intermediate struts overlap either in a circumferential direction around the stent or in an axial direction along the stent, in use, the stent movable from a first delivery position to a second placement position, in the first delivery position the stent being in an unexpanded position and having a first diameter and in the second position the stent being in a radially expanded position and having a second diameter greater than the first diameter for placement at a treatment site of a patient.

In another embodiment a stent is provided comprising: at least first, second, third and fourth spaced-apart, radially expandable rings that are substantially aligned along a longitudinal axis, each ring comprising a plurality of first struts and a plurality of second struts, the first and second struts being connected to form an undulating pattern that has peak portions and valley portions, first curved connectors joining one or more of the valley portions of the first ring to one or more of the peak portions of the second ring, the valley portions and peak portions being circumferentially offset from one another, second curved connectors joining one or more of the valley portions of the second ring to one or more of the peak portions of the third ring, the valley portions and peak portions being circumferentially offset from one another, third curved connectors joining one or more of the valley portions of the third ring to one or more of the peak portions of the fourth ring, the valley portions and peak portions being circumferentially offset from one another, a first intermediate strut extending between a first strut of the second ring to a first strut of the third ring without intersecting any of the other first and second struts and first and second curved connectors and; a second intermediate strut extending between a second strut of the third ring to a second strut of the fourth ring without intersecting any of the other first and second struts and first and second curved connectors, the first and second intermediate struts being connected to locations on the first and second struts, respectively, such that no portions of the first and second intermediate struts overlap either in a circumferential direction around the stent or in an axial direction along the stent, in use, the stent movable from a first delivery position to a second placement position, in the first delivery position the stent being in an unexpanded position and having a first diameter and in the second position the stent being in a radially expanded position and having a second diameter greater than the first diameter for placement at a treatment site of a patient.

The stents of the present invention are highly compressible and can assume compressed diameters sufficient for mounting and delivering the stents on or within small diameter delivery devices (e.g., elongate wires, catheters, etc.) while exhibiting the scaffolding, radial force, radiopacity and kink resistant properties sufficient for treatment of small diameter vessels or ducts.

BRIEF DESCRIPTION OF THE DRAWINGS

Preferred embodiments of the present disclosure are described herein with reference to the drawings wherein:

FIGS. 11A and 11B illustrate a stent in another embodiment of the present invention having struts with recesses or openings for placement of radiopaque materials or therapeutic agents.

DETAILED DESCRIPTION

Figure 2A:
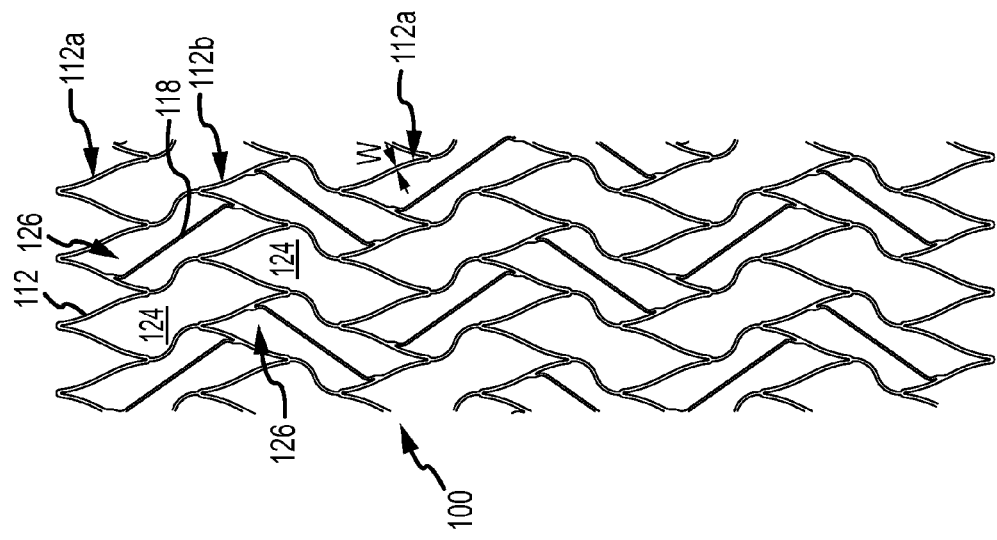
FIGS. 2A and 2B show plan views of a second embodiment of the stent of the present invention in the expanded position.

Referring now in detail to the drawings wherein like reference numerals identify similar or like components throughout the several views, several embodiments of the vascular prosthesis of the present invention are illustrated. For clarity not all like parts are labeled.

The vascular prostheses disclosed herein are preferably composed of shape memory material, such as Nitinol, and are preferably laser cut from a tube. Alternative materials such as platinum, stainless steel, bioabsorbable metals, bio-polymers and self-expanding polymers are also contemplated. The prosthesis can be treated with a radiopaque material at its ends or can have radiopaque marker bands at its ends or interspersed throughout or have a radiopaque coating over part or over the entire body of the prosthesis as described below. It can alternatively be made of a polymeric material or composed of metal with a polymeric coating or a metal coating such as platinum. A coating carrying a localized drug could also be provided.

Figure 1A:
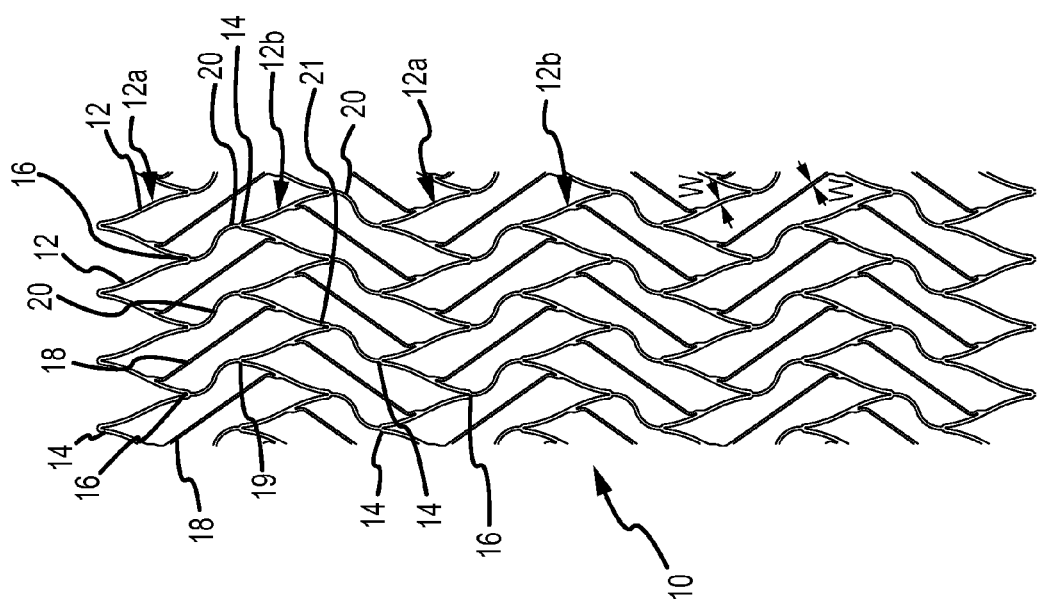
FIGS. 1A and 1B show plan views of a first embodiment of the stent of the present invention in the expanded position.

Turning first to the embodiment of FIG. 1A, the vascular prosthesis comprises a stent 10 which includes a plurality of connected rings of generally V-shaped segments comprising struts 12 with rounded vertices or peaks 14. Each ring extends radially and adjacent axially spaced rings are out of phase or staggered with respect to the adjacent axial ring. That is, the V-struts of the alternating rings 12a are substantially axially aligned, and the V-struts of the alternating rings 12b are substantially axially aligned but offset with respect to the V-struts of rings 12a.

Adjacent rings 12a, 12b are attached by curved connector struts 20. More particularly, the connector strut 20 extends from the proximal vertex 16 or valley of the V-struts 12 of ring 12a to the distal vertex 19 of the strut 12 of ring 12b, and then from the proximal vertex or valley 21 of the V-strut of ring 12b to the distal vertex of the V-strut 12 of ring 12a in a repeating pattern. The struts are curved and preferably have an elongated S-shaped curve.

Coverage or intermediate struts 18 extend from an intermediate portion of the V-strut in one ring, e.g. ring 12a, to an intermediate portion of a strut 12 in second axially adjacent ring 12b. In addition to other functions, as described below, coverage/intermediate struts 18 are designed to provide additional contact area with the vessel and provide smaller cells to limit amount of tissue entering the cells.

In one embodiment, the V-shaped struts, connector struts and coverage struts are of the same dimension. In a preferred embodiment, they each have a width w of about 0.001 inches and a wall thickness (viewed as the dimension into the paper) of about 0.002 inches. In an alternate embodiment, the struts vary in dimension such that coverage struts have a smaller width than the connector struts which have a smaller width than the V-strut. For example, in one embodiment of this varying strut dimension, the coverage strut has a dimension of about 0.001 inches, the connector strut has a dimension of about 0.0016 inches and the V-strut has a dimension of about 0.002 inches. In another embodiment, the coverage strut has a dimension of about 0.0008 inches, the connector strut has a dimension of about 0.0014 inches and the V-strut has a dimension of about 0.0018 inches.

FIG. 2A illustrates an alternate embodiment of the stent of the present invention. Stent 100 is identical to stent 10, i.e. has the same basic pattern, except that instead of coverage or intermediate struts 118 being connected to each V-strut 112 in adjacent rings 112a, 112b, i.e. extending through every cell, they are provided in an alternating pattern so that they are positioned in every other cell, i.e. in cells 126 (not in cells 124) and thereby connect every other V-strut intermediate portion. The dimensions of the struts can be the same as described in the embodiment of FIG. 1A. In the expanded configuration, a double helix pattern is formed. In an alternate embodiment, one of the rows of coverage struts is absent to form a pattern with a single helix.

Figure 3A:
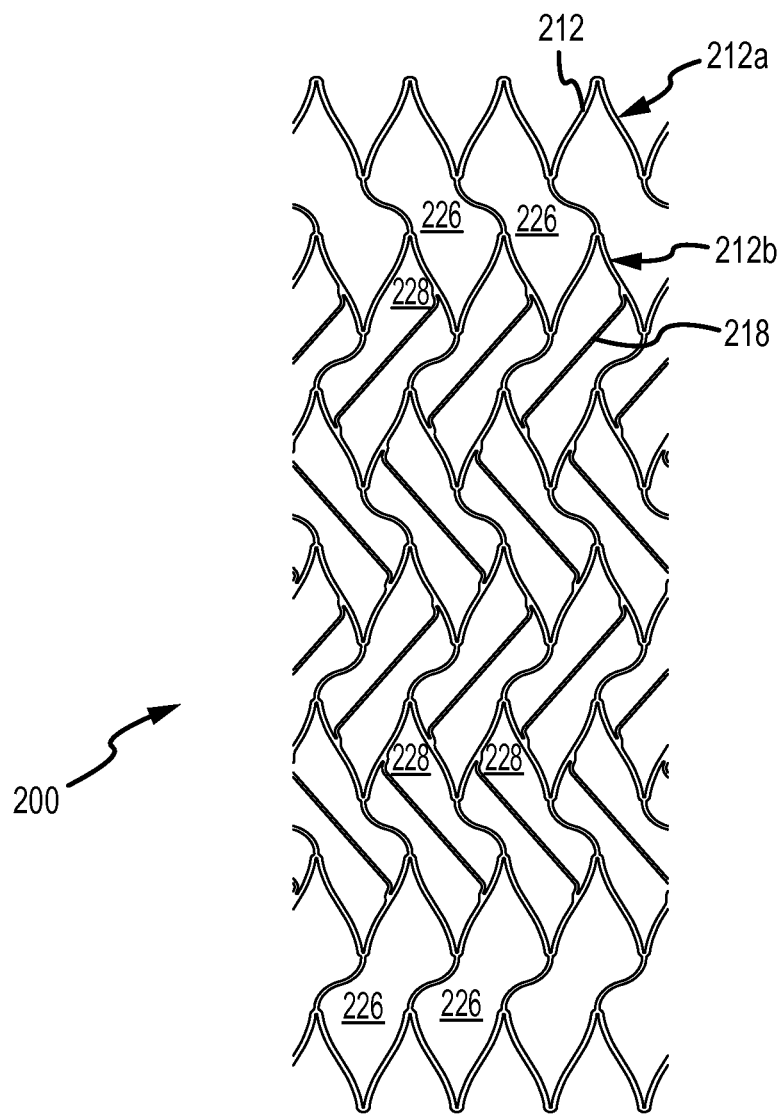
FIGS. 3A and 3B show plan views of a third embodiment of the stent of the present invention in the expanded position.

FIG. 3A illustrates an alternate embodiment of the stent of the present invention. Stent 200 is identical to stent 10 except that instead of coverage or intermediate struts 218 connecting the V-struts 212 in all adjacent rings 212a, 212b, coverage struts are absent from the proximal-most and distal-most V-struts. Thus, outermost cells 226, formed in part by the outermost rings at opposing ends of the stent, do not have coverage struts, while the remaining cells 228 have coverage struts 218 extending therein. By eliminating the coverage struts on the outer rings the radial strength is diminished to enable the stent ends to more easily compress and to more easily load into the catheter or sheath for delivery. The dimensions of the struts can be the same as described in the embodiment of FIG. 1A.

Note that the stent struts generally straighten when the stent is compressed (collapsed) inside a delivery sheath or catheter or onto a small diameter delivery device. More specifically, the stent struts are configured, dimensioned, and interconnected so that the struts are able to shift from an initial position to a second position where they are more longitudinally aligned with the longitudinal axis of the stent when the stent is collapsed to its compressed/delivered state. The stent design also accommodates nesting of the stent struts. As such the stents of the present invention may assume compressed diameters in the range of 0.010 to 0.025 inches.

Figure 1B:
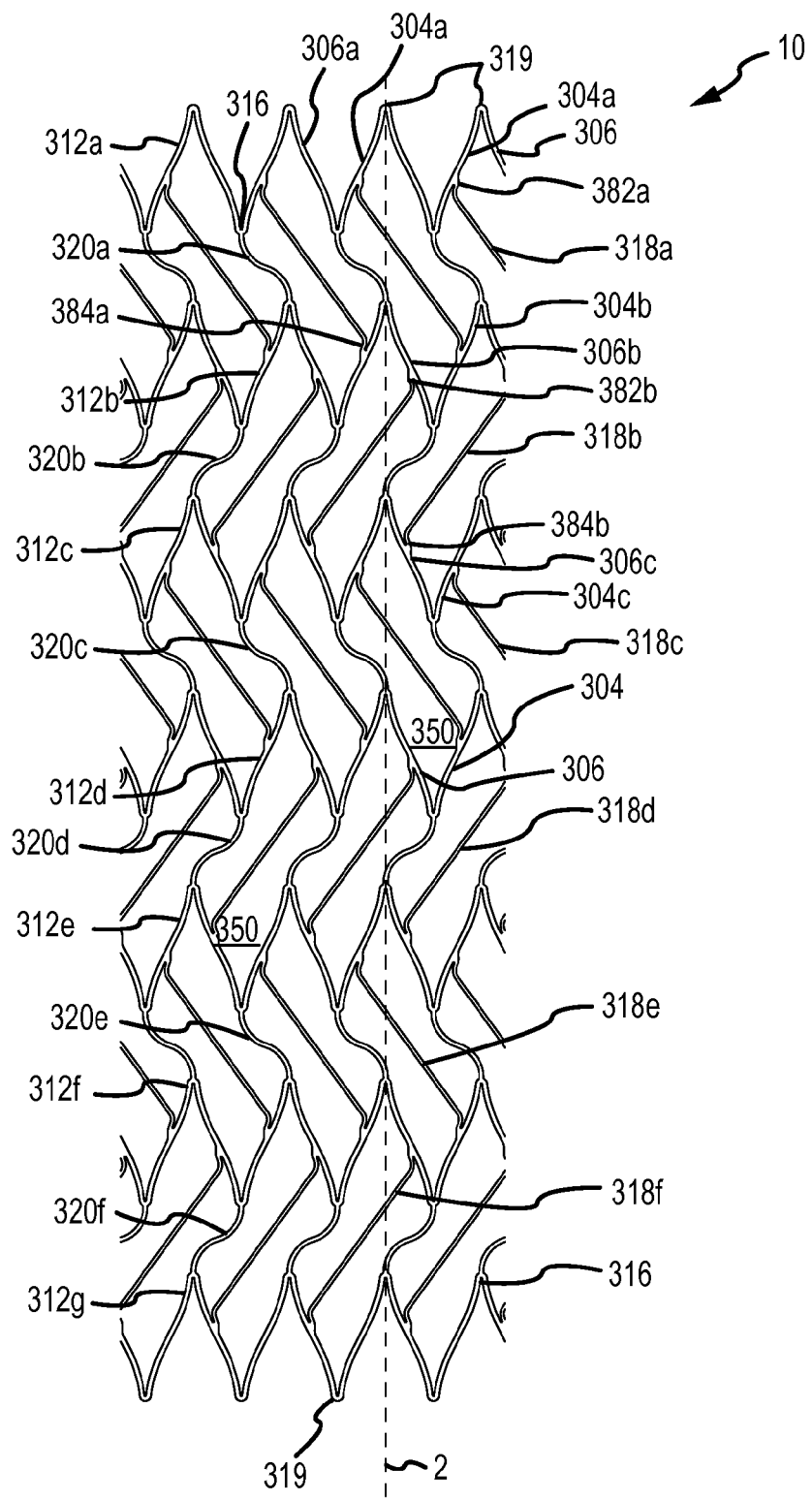
Figure 2B:
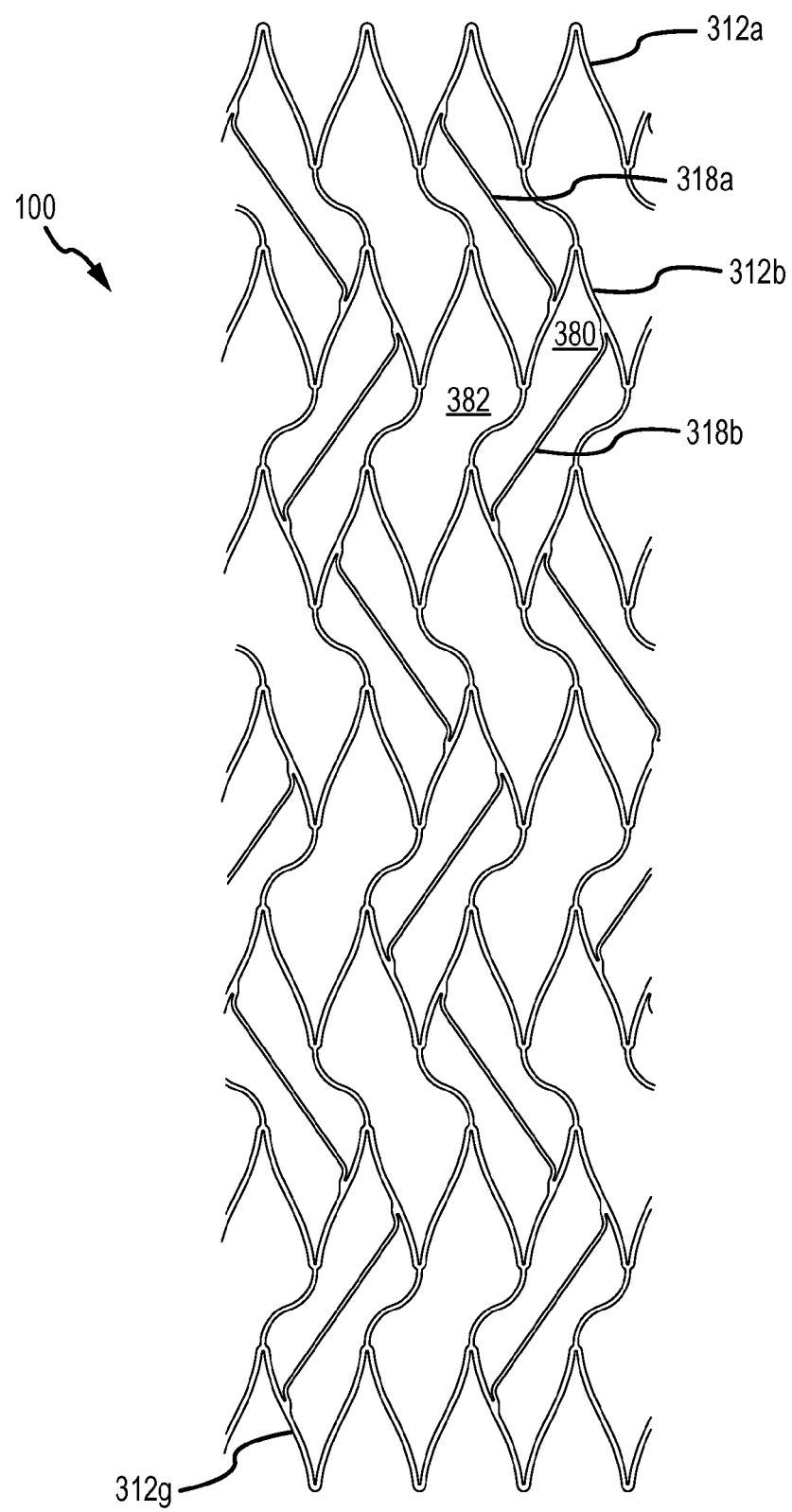
Figure 3B:
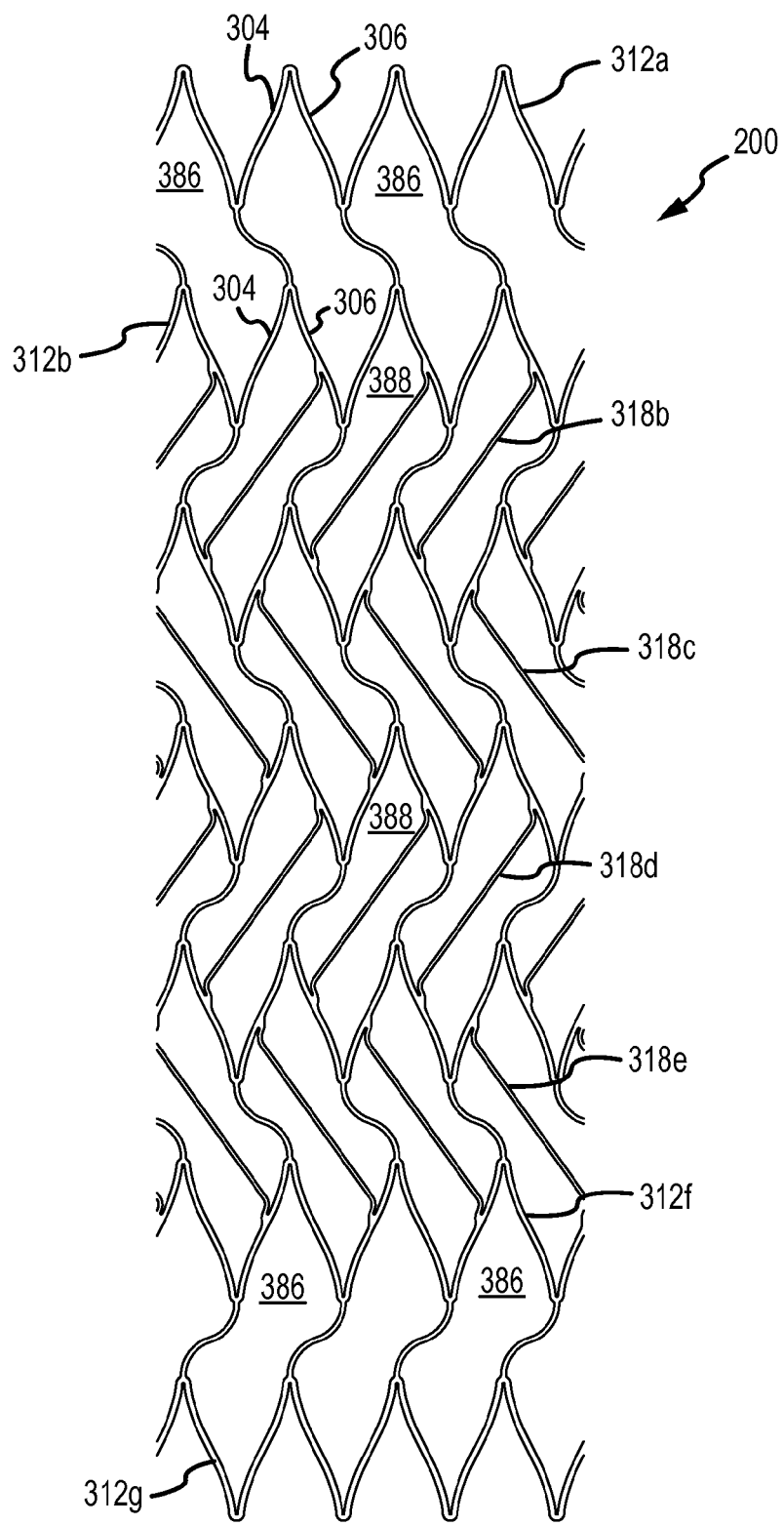

In the paragraphs that follow the stents of FIGS. 1A, 2A and 3A will be described in alternative language and with the use of different reference numbers. FIGS. 1B, 2B and 3B represent, respectively, the same stents shown in FIGS. 1A, 2A and 3A. It is important to note that although alternative language is used to describe the stents of FIGS. 1B, 2B and 3B, they are identical in form and function to the stents respectively shown in FIGS. 1A, 2A and 3A.

Figure 4:
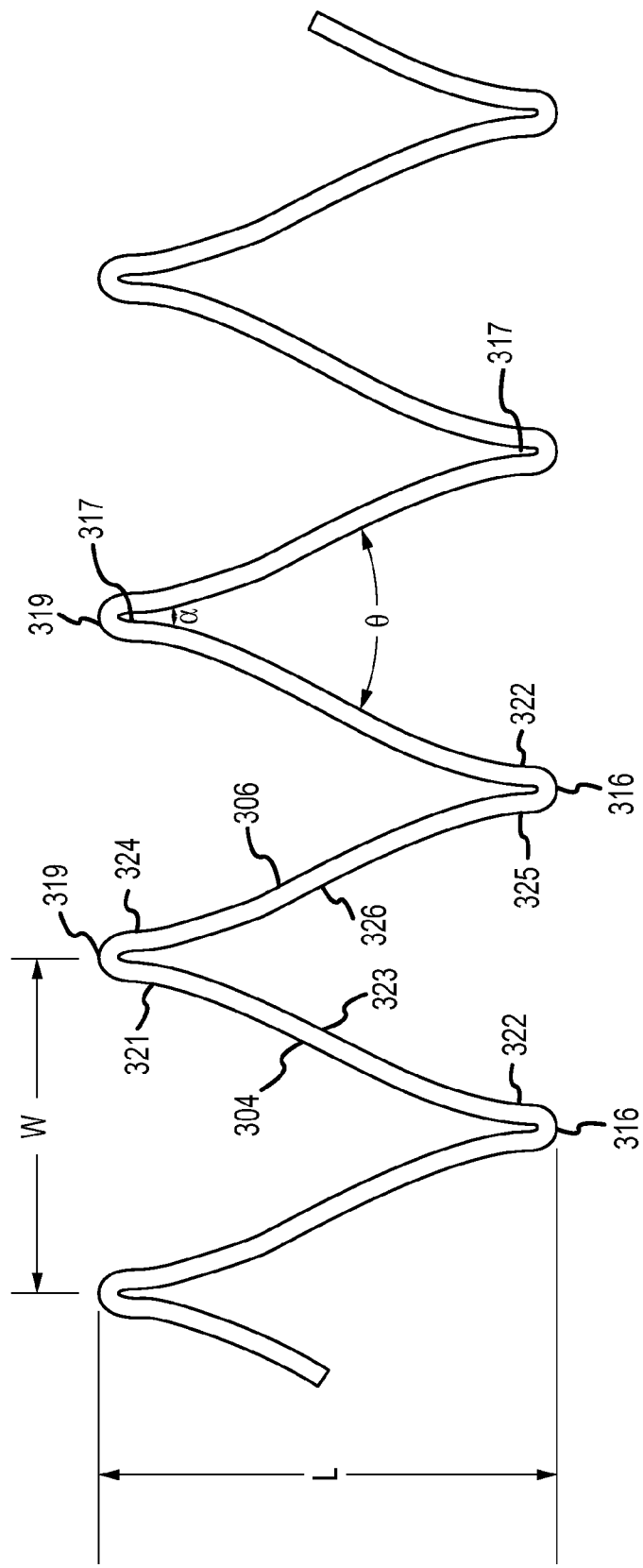
FIG. 4 depicts a ring of a stent in an embodiment of the present invention.

Turning now to FIGS. 1B and 4, stent 10 is shown comprising a plurality of spaced-apart and radially expandable rings 312a-g that are substantially aligned along a longitudinal axis 2. Each of the rings is formed by a plurality of first struts 304 and a plurality of second struts 306 that are connected to form an undulating pattern having peak portions 319 and valley portions 316. Each of the first struts 304 includes a first end segment 321, a second end segment 322, and a middle segment 323 disposed between the first and second end segments as illustrated in FIG. 4. Likewise, each of the second struts 306 includes a first end segment 324, a second end segment 325, and a middle segment 326 disposed between the first and second end segments. The first and second struts 304 and 306 are connected to form generally V-shaped patterns with end segments 321 and 324 forming peak portions 319 and end segments 322 and 325 forming valley portions 316. In one embodiment the length (L) to width (W) ratio of the generally V-shaped pattern is between about 1.2 to about 1.5, and preferably between about 1.25 to about 1.4. In a preferred embodiment, struts 304 and 306 have a curved configuration (as shown) that transitions to a generally straight configuration when the stent is compressed to its delivery position. This feature contributes to the stent's ability to assume a highly compressed/delivered state. The peak and valley portions 319 and 316 are typically rounded and have generally U-shaped, V-shaped, or similar configurations that comprise narrow slot-like portions 317. The angle α between the connected end segments of first struts 304 and second struts 306 is typically between about 0 to about 20 degrees, and preferably between about 0 to about 10 degrees while the major angle θ between the middle segments of struts 304 and 306 is between about 35 to about 55 degrees when the stent has been deployed into a recommended size vessel. The manner by which the first and second struts 304 and 306 are connected, in combination with the small angular displacement between the connected end segments of the struts, contribute to the stent's ability to be compressed to a small diameter without excessive compressive forces being applied to the stent and also minimizes stresses at the connections during compression or expansion of the stent. This is of particular importance in use with a self-expanding stent where the radial force exerted by the stent in its expanded/implanted state is directly related to the compressive force used to compress the stent.

Figure 5:
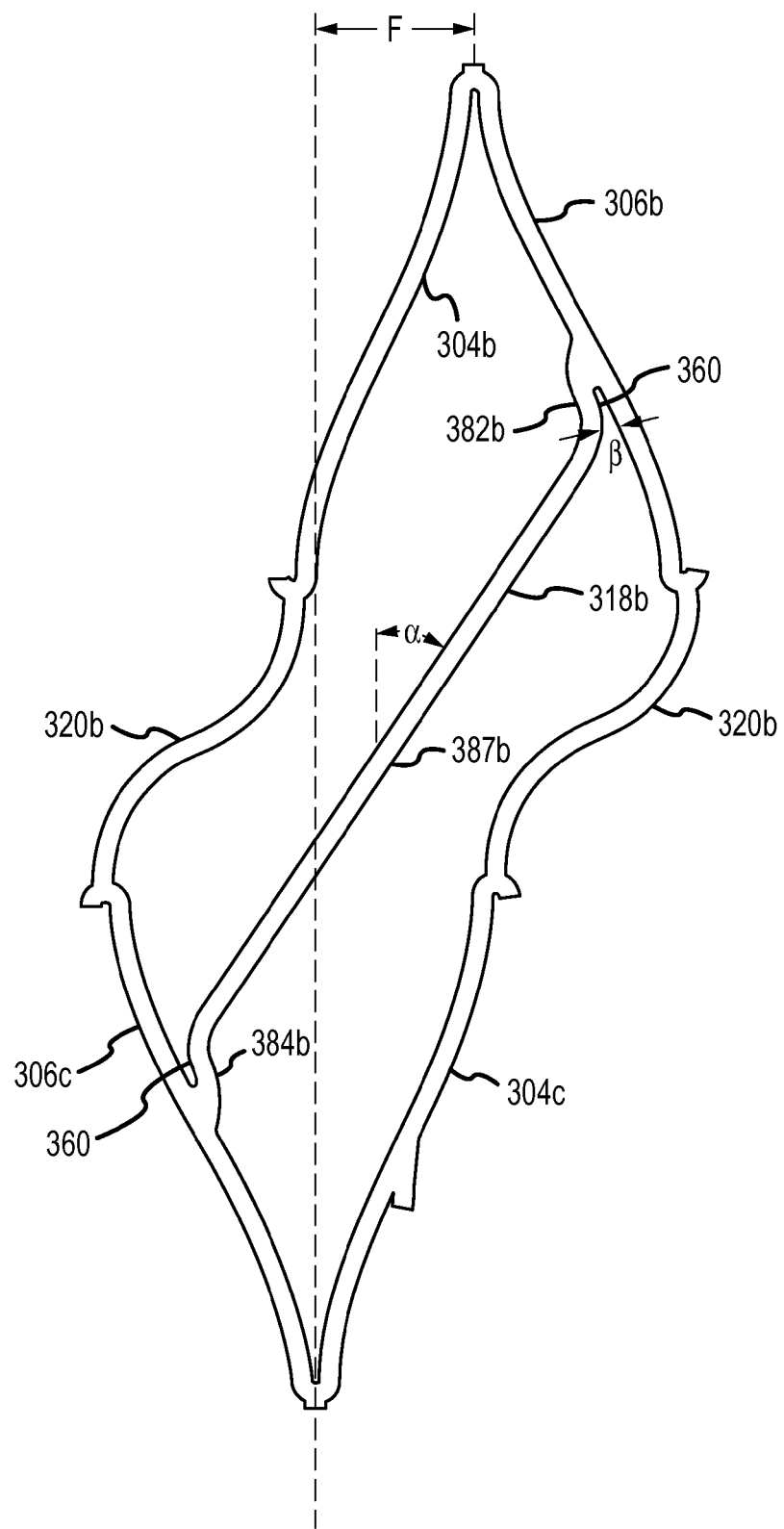
FIG. 5 depicts an enlarged view of a stent cell in an embodiment of the present invention.

As shown in FIGS. 1B and 5, the peak and valley portions 319 and 316 of adjacent rings 312 are circumferentially offset from one another by distance F. Circumferentially offsetting of rings 312a-g accommodates the nesting of stent elements as the stent is compressed, as is described below. The valley portions 316 and peak portions 319 of adjacent rings 312a-g are connected by connectors 320a-f. The connectors are typically curved (U-shaped, C-shaped, S-shaped, omega-shaped, undulating, etc.) and preferably have a generally S-shaped configuration. In the embodiment of FIG. 1B, each of the valley and peak portions 316 and 319 of adjacent rings 312 are connected. An advantage of this connection scheme is that it inhibits or limits the peak and valley portions from flaring outside the cylindrical plane of the stent to enhance the retractability of the stent into a sheath, delivery catheter, or the like, after it has been deployed or partially deployed within the lumen of a patient. In alternative embodiments, particularly in balloon expandable stents and in applications where retraction of the stent is not important, not every valley and peak portion of adjacent rings is connected. In these embodiments connectors 320 may be selectively omitted to enhance stent flexibility and/or provide larger openings in the stent wall to permit passage of other intraluminal treatment devices (e.g., embolic coil delivery devices, guidewires, catheters, stent delivery systems, etc.).

In one embodiment, the longitudinal distance between adjacent undulating rings 312 is about the same as the offset distance, F, with the radius of curvature of the curved portion (s) of connectors 320 being about one half the offset distance, that is about 0.5F. This arrangement enables a high degree of stent compression by enabling connectors 320 to elongate and assume a thinner radial profile and, in doing so, to become more aligned with the longitudinal axis of the stent during stent compression.

Intermediate struts 318a-f are connected to and situated between adjacent rings 312a-g. The intermediate struts 318 provide a number of advantages. They 1) provide additional surface area to enhance the stent's scaffolding function to inhibit prolapse of tissue into the interior of the stent, 2) increase the stent's radial strength, and 3) inhibit kinking and/or buckling of the stent as it is delivered through the tortuous anatomy of a patient. As exemplified in FIG. 5 with respect to an intermediate strut 318b extending between ring 312b and 312c, intermediate struts 318 comprise first and second end sections 382 and 384 (382b and 384b in FIG. 5), respectively, and a middle section 386 (386b in FIG. 5). As shown in FIG. 1B, a first set of intermediate struts 318a extend between and are connected to the first struts 304 of the first and second rings 312a and 312b without intersecting any of the stent's other first and second struts or curved connectors. As shown, the first ends 382a are connected to the first struts 304a of ring 312a and the second ends 384a are connected to the first struts 304b of ring 312b. A second set of intermediate struts 318b, having a slope opposite to the slope of intermediate struts 318a, are disposed between the second ring 312b and the third ring 312c with the first ends 382b being connected to the second struts 306b of ring 312b and the second ends 384b being connected to the second struts 306c of ring 312c. In a preferred embodiment, as shown, the intermediate struts 318a and 318b are connected at locations along the first struts 304 and second struts 306, respectively, such that no portions of the first and second intermediate struts overlap either in the circumferential direction around the stent nor in the axial direction along the stent. Intermediate struts 318c-f are further provided in a similar repeating pattern between rings 312d-g as illustrated in FIG. 1B. Although the middle section 387 of struts 318 is preferably straight, it may comprise other shapes. For example, middle section 387 may comprise any other shape that is capable of straightening configuration when the stent is compressed into or onto a small diameter delivery device. In alternative embodiments one or more intermediate struts 318 may be omitted from the stent structure to obtain a desired radial stiffness and/or to provide larger stent openings that permit passage of other intraluminal treatment devices.

In one embodiment, the connection between the intermediate struts 318 with the first and second struts 304 or 306 has a generally wish-bone configuration that comprises a narrow slot-like portion 360. Other connection configurations are contemplated, such as U-shaped, V-shaped, or the like. The angle β between end sections 382 and 384 and the first and second struts 304 and 306 (See FIG. 5) is generally between about 0 to about 20 degrees, and preferably between about 0 to about 10 degrees. As described above in conjunction with connection at the peak and valley portions 319 and 316 of struts 304 and 306, this method of attachment contributes to the stent's ability to be compressed to a small diameter without excessive compressive forces being applied to the stent and minimizes stresses at the connections during compression or expansion of the stent.

The stent 10 of FIG. 1B illustrates a stent having seven rings 312, with each ring comprising four peak portions 319 and four valley portions 316. It is appreciated, however, that stent 10 may comprise fewer or more undulating rings 312 and that the rings 312 may comprise fewer or more peak and valley portions. For example, in a larger diameter stent rings 312 will typically have a greater number of undulations, that is a larger number of peak and valley portions. Moreover, to increase or decrease the length of the stent fewer or greater number of rings 312 may be used. With respect to the embodiment of FIG. 1B, the peak and valley portions 319 and 316 of adjacent rings 312 may be offset by about 0 to 45 degrees and preferably by about 45 degrees. In stents having a greater number of peak and valley portions, the adjacent rings 312 will be circumferentially offset by a smaller amount. For example, in stents having six peak and valley portions 319 and 316 adjacent rings 312 will generally be circumferentially offset by greater than 0 degrees to about 30 degrees and preferably by about 30 degrees. In stents having five peak and valley portions 319 and 316 adjacent rings 312 will generally be circumferentially offset by greater than 0 degrees to about 36 degrees and preferably by about 36 degrees. The degree by which adjacent rings 312 are circumferentially offset and the location and manner in which the intermediate struts 318 are attached to the first and second struts 304 and 306 will primarily establish the angular orientation of the intermediate struts 318 within the stent structure. The angular orientation, or slope y, of the intermediate struts 318 will affect the stent's ability to be compressed to small diameters. For example, an excessively large slope y will adversely impact the stent's ability to be compressed. In one embodiment, stent 10 is configured so that the intermediate struts 318 have a slope y between about 25 to about 45 degrees and preferably between about 30 to about 40 degrees.

Figure 6:
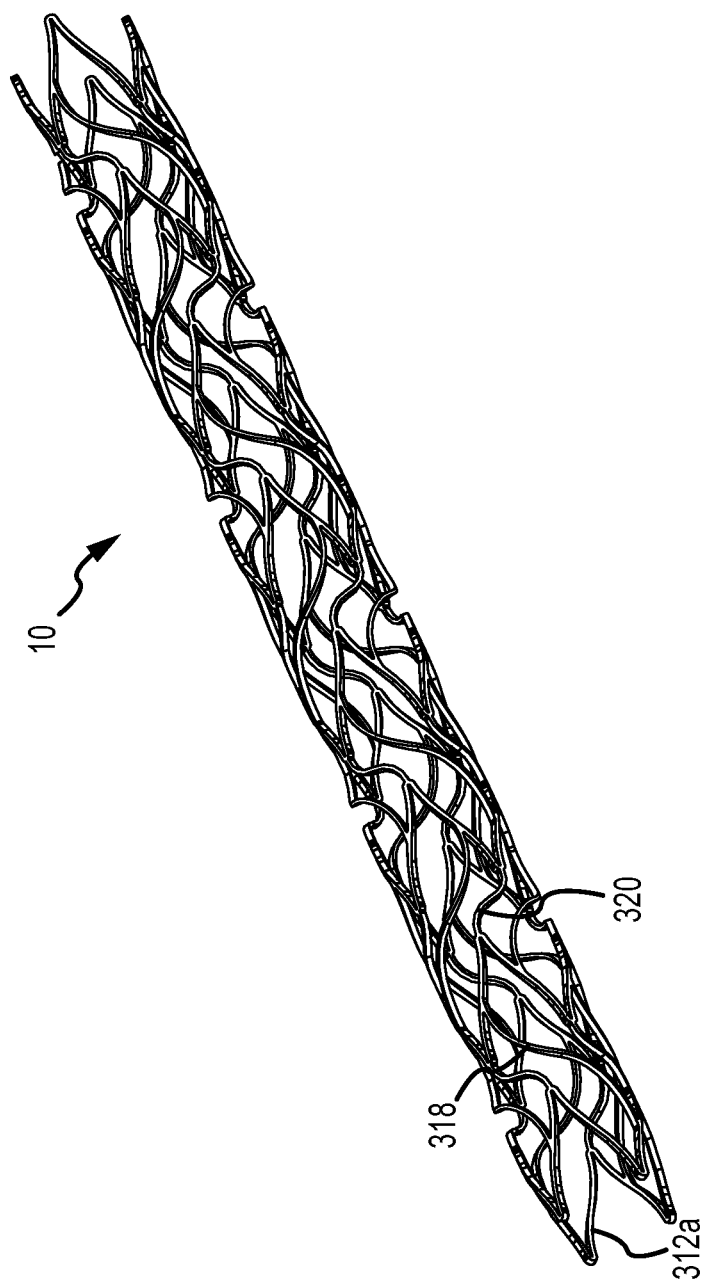
FIG. 6 is an isometric view of the stent shown in FIG. 1.
Figure 7:
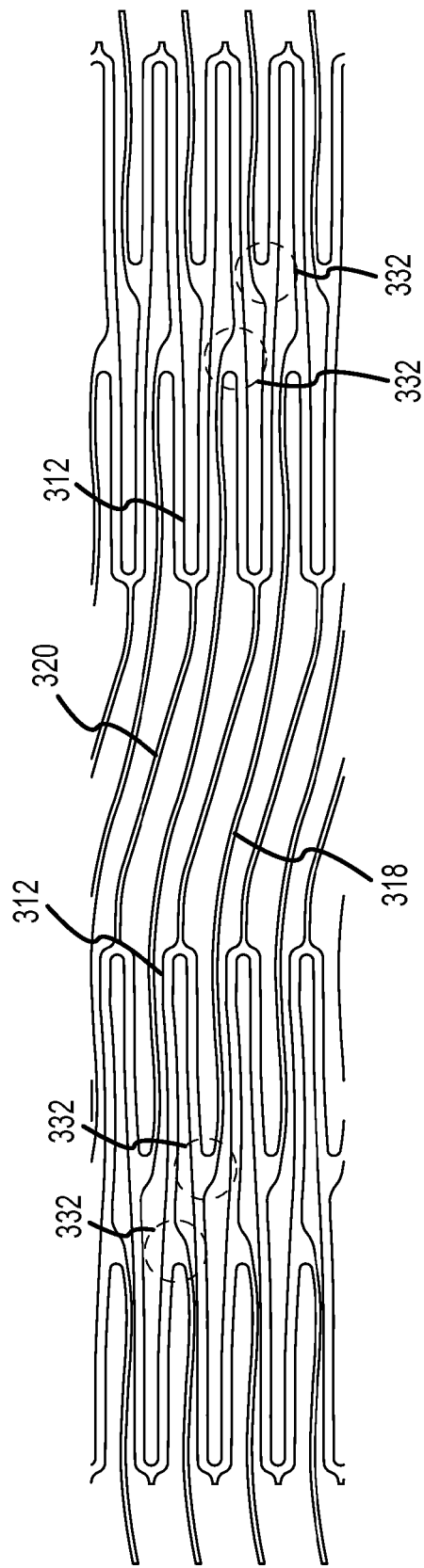
FIG. 7 shows a portion of the stent of FIG. 1 in a compressed/delivered state.
Figure 8:
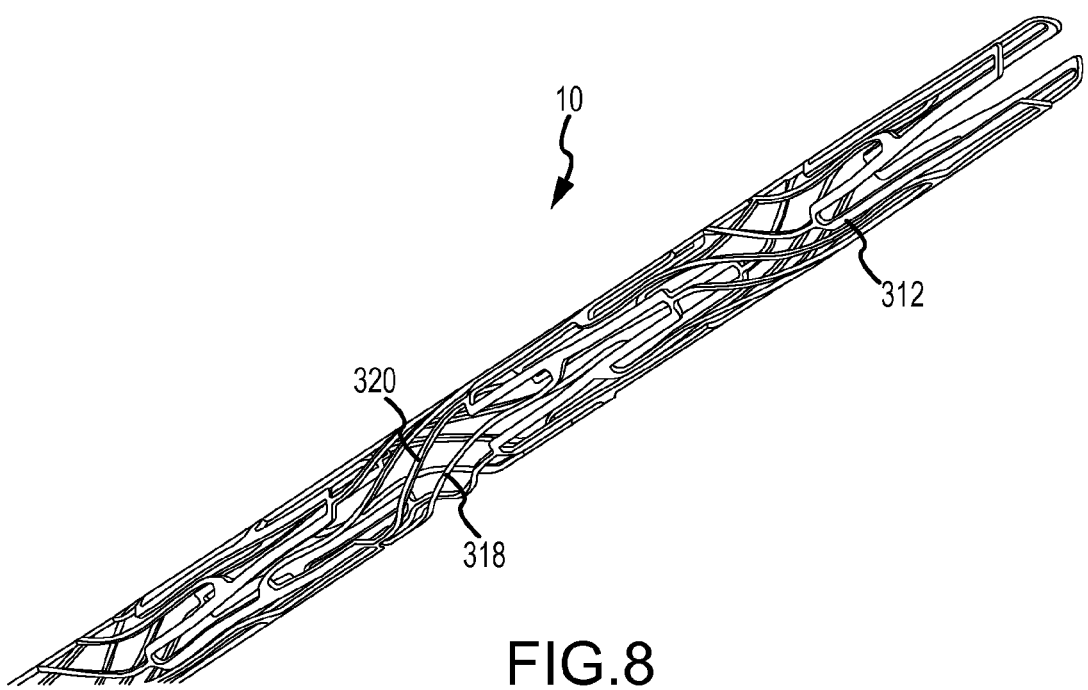
FIG. 8 is an isometric view of the stent of FIG. 1 in a compressed/delivered state.

FIG. 6 is an isometric view of stent 10 depicted in FIGS. 1A and 1B. FIG. 7 illustrates a portion of stent 10 in a compressed state and ready for delivery on a small diameter delivery device (e.g., elongate wire) and/or within the lumen of a small diameter catheter. FIG. 8 shows an isometric view of a portion of stent 10 in a compressed state. As discussed above, and as shown in FIGS. 7 and 8, a combination of stent features permit the stent to be compressed to a small diameter. The circumferential offset of rings 312 enables the stent elements to shift to become more longitudinally aligned with the longitudinal axis 2 of the stent as the stent is compressed. Note also that the manner in which the intermediate struts 318 are connected to rings 312 results in a staggered placement of the bulkier connection points 332 so that no two adjacent connection points 332 are circumferentially aligned with one another when the stent is compressed to its delivery position. This permits stent 10 to obtain a smaller compressed diameter and also facilitates nesting of the stent elements as discussed above. An important feature of stent 10 is that none of the stent elements overlap with one another when the stent is in its compressed/delivered state. Overlapping stent struts in the delivered state are undesirable because they adversely affect the flexibility of the stent during delivery, increase the delivered diameter of the stent, and create an uneven (non-smooth) outer wall surface.

Figure 9A:
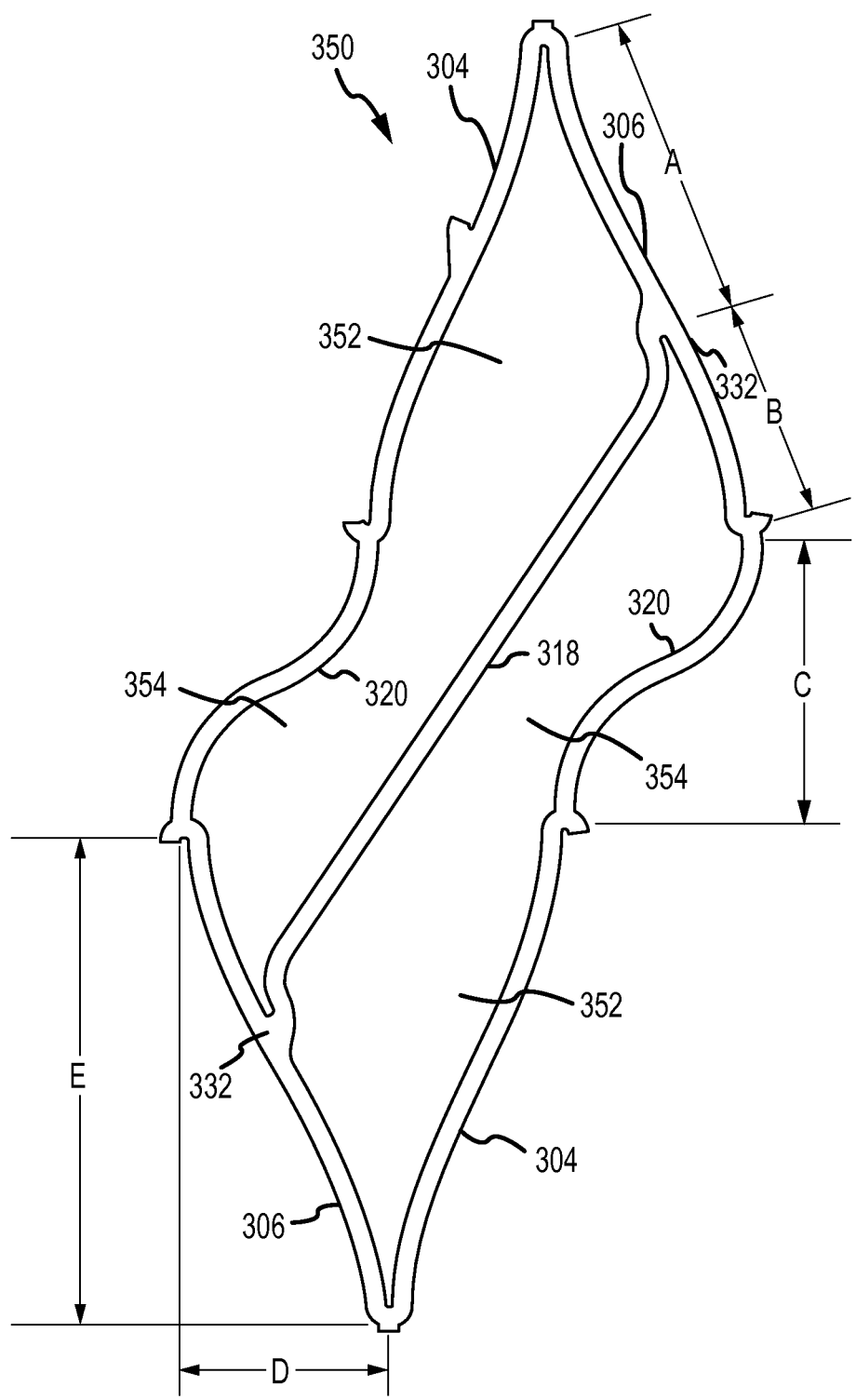
FIG. 9A illustrates a cell of a stent in one embodiment of the present invention.

FIG. 9A depicts an exemplary cell 350 of stent 10 comprising ring struts 304 and 306, connector struts 320 and intermediate strut 318. As described above, in one embodiment ring struts 304 and 306, connector struts 320 and intermediate struts 318 are of the same width and thickness. In other embodiments the struts vary in dimension such that intermediate struts 318 have a smaller width than the connector struts 320 which have a smaller width than the ring struts 304 and 306. Generally, the width and thickness of the ring struts, connector struts and intermediate struts are between about 0.0008 to about 0.003 inches and 0.001 to about 0.003 inches respectively and preferably between 0.0008 to about 0.002 inches and 0.0018 to about 0.0022 inches, respectively. The width of intermediate strut 318 is typically smaller than the width of ring struts 304 and 306. A reduced width dimension of intermediate strut 318 enables the stent to assume a smaller compressed diameter without appreciably affecting the strut's scaffolding function. To enhance stent flexibility, the width of connector struts 320 is also typically smaller than the width of ring struts 304 and 306. The thickness of the struts may also vary to achieve certain desired stent characteristics (e.g., radial force, anti-kinking, etc.).

With continued reference to FIG. 9A the placement of the connection points 332 of intermediate strut 318 is shown relative to dimension A and dimension B of ring struts 304 and 306. An important aspect of the present invention is that dimension A is greater than dimension B. This dimensional relationship has several advantages. As previously described, it results in a staggered placement of connection points 332 so that no two adjacent connection points 332 are circumferentially aligned with one another. In addition, it creates a cell structure 350 having areas of larger openings 352 and smaller openings 354, the smaller opening 354 contributing more significantly to the prevention of tissue prolapse into the interior of the stent, the larger openings 352 providing regions sufficiently large to permit passage of other intraluminal treatment devices (e.g., embolic coil delivery devices, guidewires, catheters, stent delivery systems, etc.) In one embodiment dimensions A, B, C, D and E are 0.0643 inches, 0.0405 inches, 0.0631 inches, 0.0773 inches and 0.0974 inches, respectively, with larger openings 352 having a diameter of about 0.04 inches.

Figure 9B:
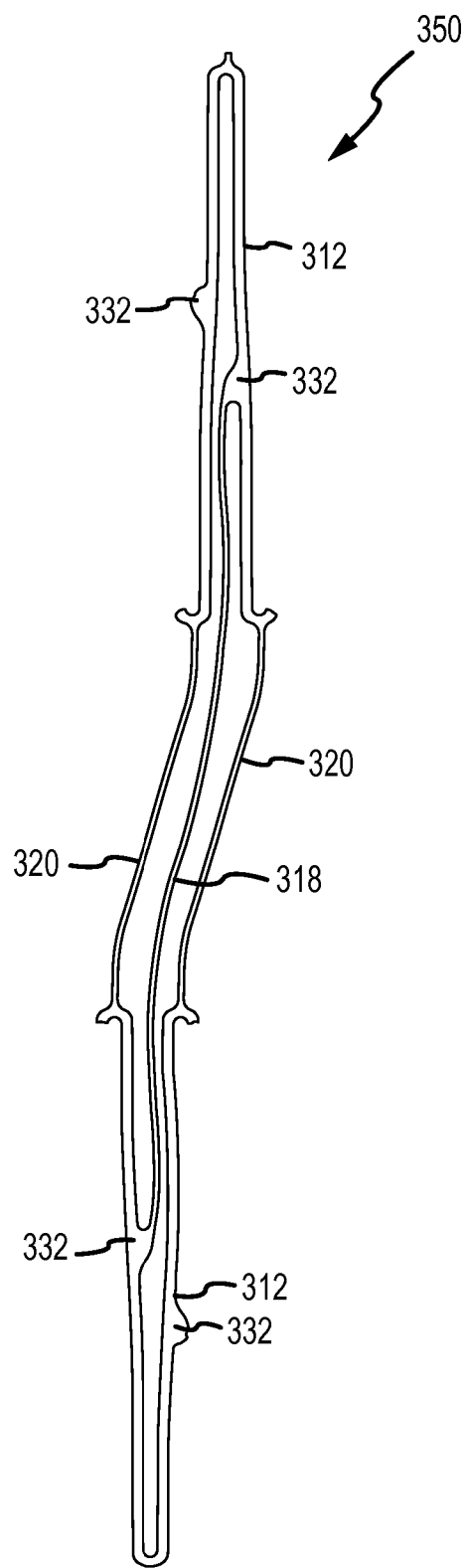
FIG. 9B illustrates the cell of FIG. 9A in a compressed configuration after loading the stent onto or within a small diameter delivery device.

FIG. 9B shows the stent cell 350 of FIG. 9A with the stent 10 in its compressed/delivered state. As shown, the cell is highly compressible at least in part by the stent elements ability to shift during stent compression so that they nest and become more longitudinally aligned with the longitudinal axis 2 of the stent and by the manner in which the intermediate struts 318 are connected to rings 312.

Figure 10:
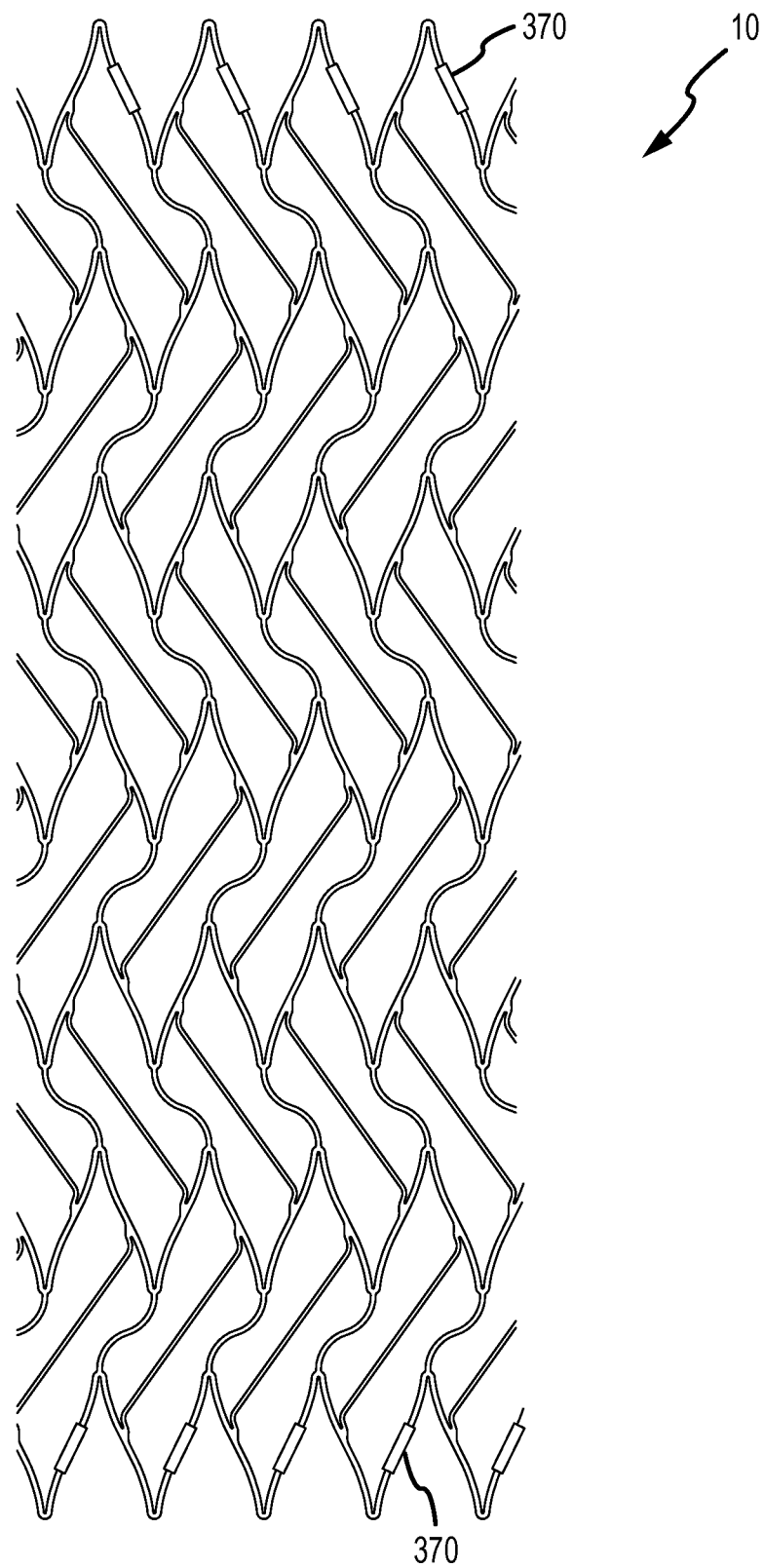
FIG. 10 illustrates a stent in another embodiment of the present invention having radiopaque marker bands.
Figure 12:
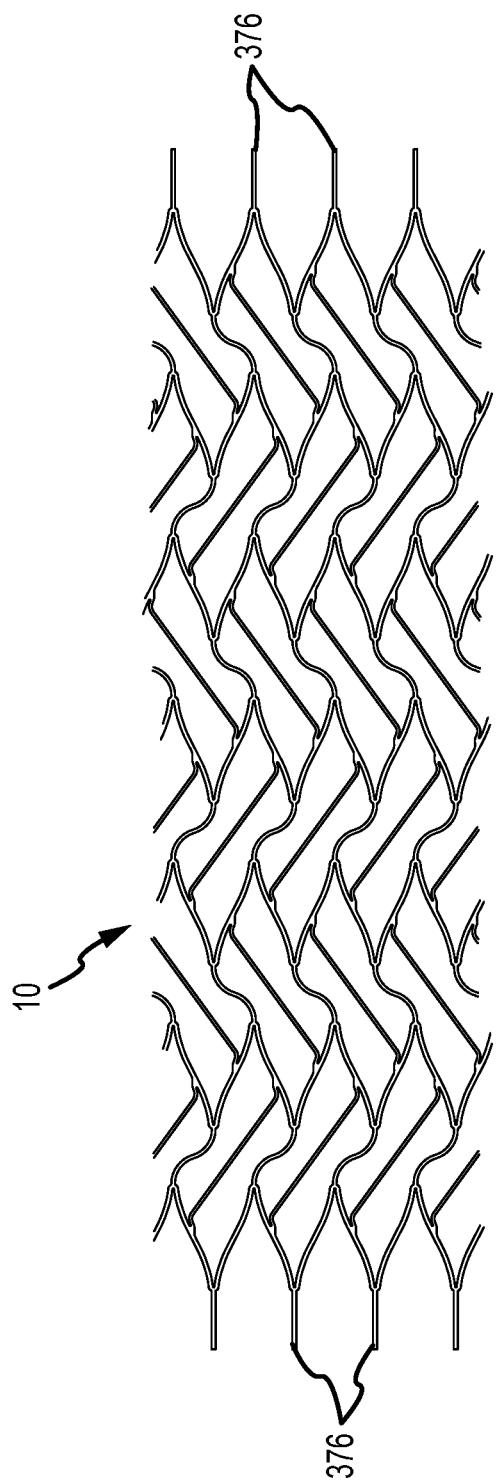
FIG. 12 illustrates a stent in another embodiment of the present invention.
Figure 13:
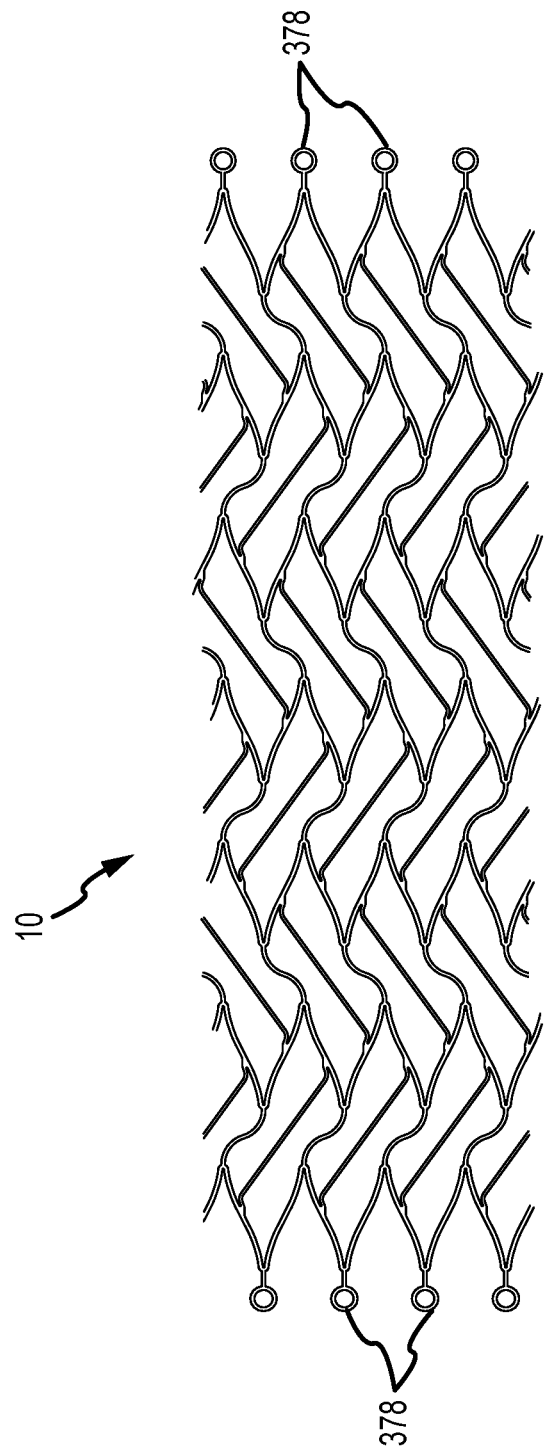
FIG. 13 illustrates a stent in another embodiment of the present invention.

To enhance the radiopacity of the stent under fluoroscopy the outer surface of stent 10 may include a coating or cladding of a highly radiopaque material such as platinum, gold, palladium, tantalum, tungsten, etc. In one embodiment the surface of the stent is coated with a doped polymer containing a radiopaque material. In other embodiments additional features for attaching, embedding or otherwise incorporating highly radiopaque materials into the stent structure are provided. For example, radiopaque marker bands 370 may be attached to the end rings 312 of stent 10 as depicted in FIG. 10. Alternatively, one or more of the stent struts (304, 306, 320 or 318) may include recesses or openings for placement of a radiopaque material and/or therapeutic agents (e.g., agents for inhibiting restenosis). For the purpose of illustration FIGS. 11A and 11B shows stent 10 having openings or recesses 374 in the connector struts 320. In the embodiment of FIG. 12 stent 10 includes a plurality of struts or posts 376 extending outwardly and longitudinally from the vertices of the end rings 312. The posts 376 may themselves comprise a highly radiopaque material or may be used for attachment of radiopaque markers, such as radiopaque coils, bands (not shown) and the like. In yet another embodiment slotted stent elements 378 are provided at one or both stent ends of the stent structure, as shown in FIG. 13, for receiving and attaching radiopaque disks or the like.

FIG. 2B illustrates an alternate embodiment of the stent of the present invention. Stent 100 is substantially identical to stent 10, i.e. has the same basic pattern, except that instead of coverage or intermediate struts 318 connecting each ring 312 in adjacent rings 312*a*, 312*b*, i.e. extending through every cell, they are provided in an alternating pattern so that they are positioned in every other cell, i.e. in cells 380 (not in cells 382) to form a double helix pattern. The dimensions of the struts can be the same as described in the embodiment of FIG. 1B. In alternate embodiments, individual intermediate struts 318, or groups of intermediate struts 318, may be selectively omitted to achieve desired stent performance or function objectives.

Figure 3C:
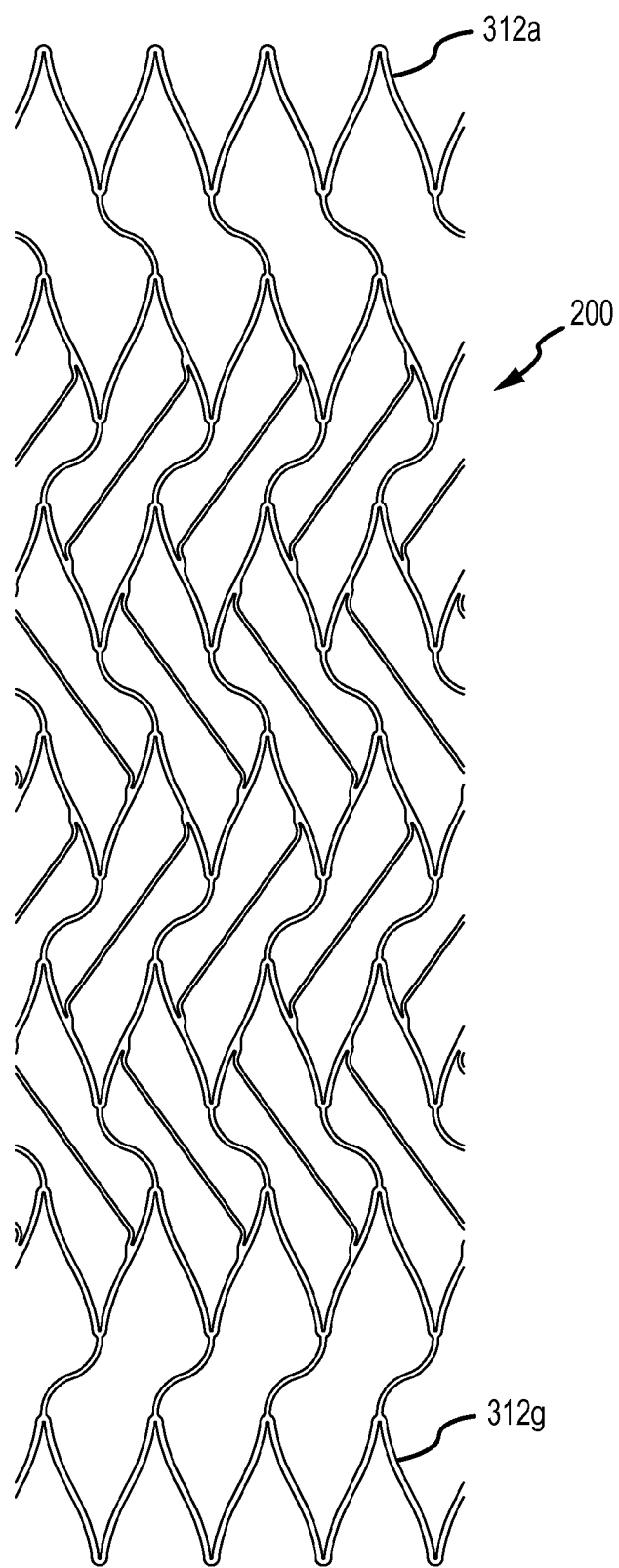
FIG. 3C illustrates a stent in another embodiment of the present invention.

FIG. 3B illustrates another embodiment of the stent of the present invention. Stent 200 is identical to stent 10 except that instead of coverage or intermediate struts 318 connecting the struts 304 or 306 in all adjacent rings 312, intermediate struts 318 are absent from the proximal-most and distal-most rings. Thus, outermost cells 386, formed in part by the outermost rings at opposing ends of the stent, do not have intermediate struts 318, while the remaining cells 388 have intermediate struts 318 extending therein. By eliminating the intermediate struts on the outer rings the radial strength is diminished to enable the stent ends to more easily compress and to more easily load into a catheter or sheath for delivery. In one embodiment, intermediate struts 318 are omitted at only one end of the stent. The dimensions of the struts can be the same as described in the embodiment of FIG. 1B. However, in alternative embodiments, end rings 312*a* and 312*g* may have widths and/or thicknesses greater than those of rings 312*b-f*, as shown in FIG. 3C, to recuperate at least some of the radial strength lost by exclusion of the intermediate struts 318 from the end portions of the stent.

Figure 14:
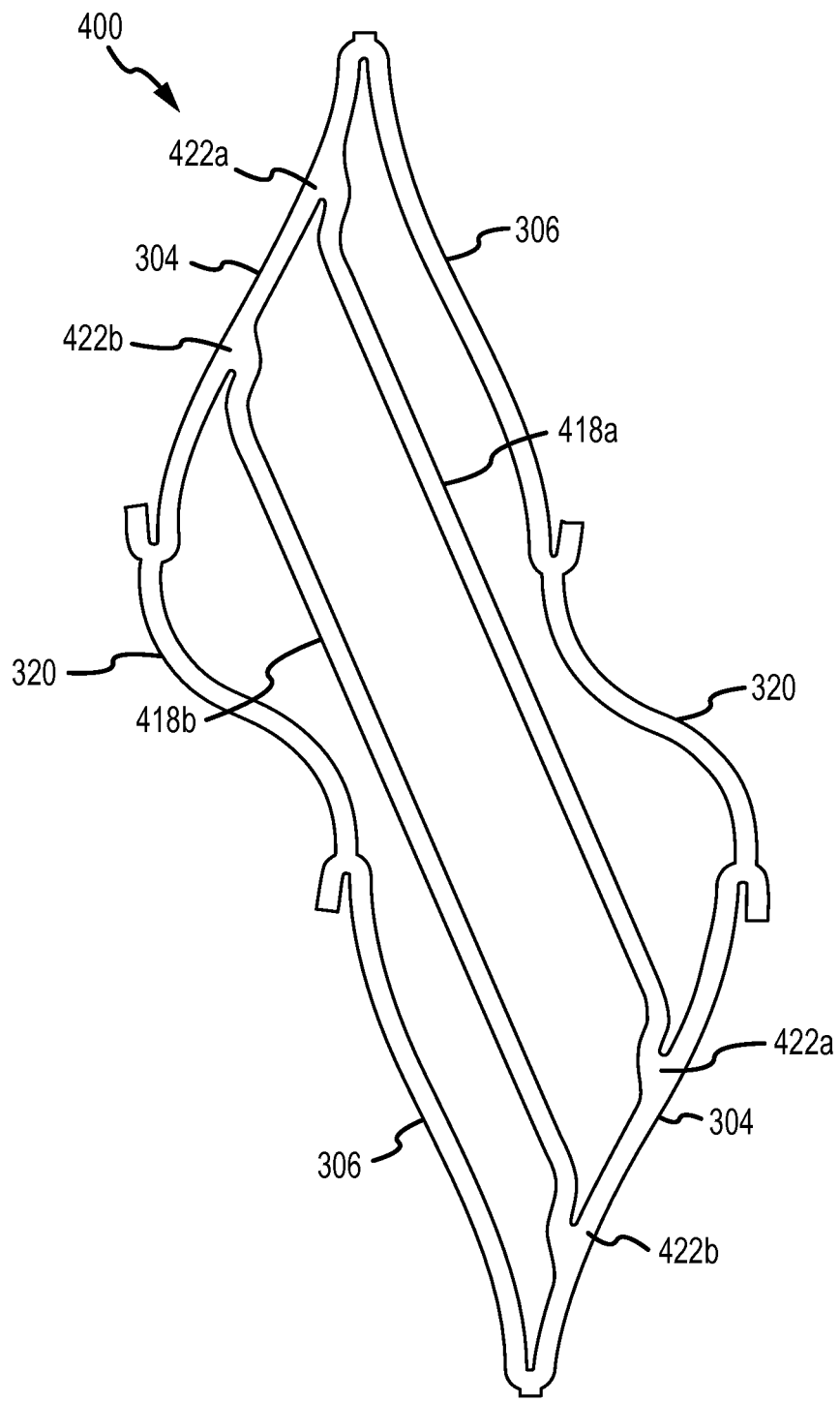
FIG. 14 illustrates a stent cell in another embodiment of the present invention.

FIG. 14 illustrates an exemplary stent cell 400 in an alternative embodiment of the present invention. Similar to the stent cell 350 described above, cell 400 comprises ring struts 304 and 306 and connector struts 320. However, instead of having one intermediate strut, cell 400 includes two intermediate struts 418*a* and 418*b* that are connected to ring struts 304 at connection points 422*a* and 422*b*, respectively. Note that cells having greater than two intermediate struts are also contemplated and that the width and/or thickness of the two or more intermediate struts may differ. Intermediate struts 418*a* and 418*b* are connected to ring struts 304 so that the connections points 422*a* and 422*b* are not circumferentially aligned with one another when the stent 10 is in a compressed state. In a preferred embodiment, the connection points 422*a* and 422*b* of intermediate struts 418*a* and 418*b* in adjacent cells are staggered so that no two adjacent connection points are circumferentially aligned with one another. In one embodiment, all of the cells of stent 10 comprise the cell structure 400. In alternative embodiments, only some of the cells comprise cell structure 400. For example, in one embodiment, only the cells located at the stent ends comprise cell structure 400, while in other embodiments cell structure 400 is interposed between cells having no intermediate struts and/or cell structures having only one intermediate strut (i.e., cell 350 as shown in FIG. 9A). An advantage of the present invention is that it enables localized control of radial strength, scaffolding, radiopacity, and other stent properties by the use of one or more of cells 350, cells 400, or cells having no intermediate struts, and any combination thereof. In preferred embodiments, the connection points of the intermediate struts of adjacent cells 400 and 350 are positioned such that that no two adjacent connection points are circumferentially aligned with one another.

While the above description contains many specifics, those specifics should not be construed as limitations on the scope of the disclosure, but merely as exemplifications of some preferred embodiments thereof. For example, vascular prosthesis dimensions other than those listed above are contemplated. Those skilled in the art will envision many other possible variations that are within the scope and spirit of the disclosure.

What is claimed is:
1. A stent comprising:
at least first, second and third spaced-apart, radially expandable rings that are substantially aligned along a longitudinal axis, each ring comprising a plurality of first struts and a plurality of second struts, the first and second struts being connected to form an undulating pattern that has peak portions and valley portions,
first curved connectors joining one or more of the valley portions of the first ring to one or more of the peak portions of the second ring, the valley portions and peak portions being circumferentially offset from one another, second curved connectors joining one or more of the valley portions of the second ring to one or more of the peak portions of the third ring, the valley portions and peak portions being circumferentially offset from one another, a first intermediate strut extending between a first strut of the first ring to a first strut of the second ring without intersecting any of the other first and second struts and first and second curved connectors and;

a second intermediate strut extending between a second strut of the second ring to a second strut of the third ring without intersecting any of the other first and second struts and first and second curved connectors, in use, the stent movable from a first delivery position to a second placement position, in the first delivery position the stent being in a fully unexpanded position and having a first diameter and in the second position the stent being in a radially expanded position and having a second diameter greater than the first diameter for placement at a treatment site of a patient;

wherein the first and second intermediate struts are connected to locations on the first and second struts, respectively, such that no portions of the first and second intermediate struts overlap either in a circumferential direction around the stent or in an axial direction along the stent when the stent is in the fully unexpanded position.

2. The stent of claim 1 comprising a plurality of first intermediate struts with one first intermediate strut extending between each of the first struts of the first ring to a first strut of the second ring without intersecting any of the other first and second struts or first and second curved connectors.

3. The stent of claim 1 comprising a plurality of second intermediate struts with one second intermediate strut extending between each of the second struts of the second ring to a second strut of the third ring without intersecting any of the other first and second struts or first and second curved connectors.

4. The stent of claim 1 comprising a plurality of first intermediate struts and a plurality of second intermediate struts, one of the first intermediate struts extending between each of the first struts of the first ring to a first strut of the second ring, one of the second intermediate struts extending between each of the second struts of the second ring to a second strut of the third ring, the first and second intermediate struts extending between and attached to the first and second struts without intersecting any of the other first and second struts or first and second curved connectors.

5. The stent of claim 1 wherein the first and second intermediate struts have a width that is less than the width of the first and second struts.

6. The stent of claim 1 wherein the first and second intermediate struts have a thickness that is less than the thickness of the first and second struts.

7. The stent of claim 1 wherein the width of the first and second struts is greater than the width of the connector struts, the width of the connector struts being greater than the width of the intermediate struts.

8. The stent of claim 1 wherein the thickness of the first and second struts is greater than the thickness of the connector struts, the thickness of the connector struts being greater than the thickness of the intermediate struts.

9. The stent of claim 1 wherein the first and second intermediate struts each comprise a first end section, a second end section and a middle section located between the first and second end sections, the middle section having a curved configuration.

10. The stent of claim 1 wherein the first and second intermediate struts each comprise a first end section, a second end section and a middle section located between the first and second end sections, the middle section having a substantially straight configuration when the stent is in the fully unexpanded position.

11. The stent of claim 10 wherein the first and second intermediate struts are connected to the first and second struts, respectively, so that the slope of the first and second intermediate struts is between about 25 to 45 degrees.

12. The stent of claim 1 wherein the first and second intermediate struts each comprise a first end section, a second end section and a middle section located between the first and second end sections, the attachment angle between the first and second end sections and the first and second struts being between about 0 and 20 degrees.

13. The stent of claim 1 wherein the connected first and second struts form a generally V-shaped pattern having a length to width ratio of between about 1.2 to 1.5.

14. The stent of claim 1 wherein the first, second and third rings each comprise four peak portions and four valley portions, the valley portions of the first ring and the peak portions of the second ring being circumferentially offset from one another by approximately 45 degrees, the valley portions of the second ring and the peak portions of the third ring being circumferentially offset from one another by approximately 45 degrees.

15. The stent of claim 1 wherein the first, second and third rings each comprise five peak portions and five valley portions, the valley portions of the first ring and the peak portions of the second ring being circumferentially offset from one another by approximately 36 degrees, the valley portions of the second ring and the peak portions of the third ring being circumferentially offset from one another by approximately 36 degrees.

16. The stent of claim 1 wherein the first, second and third rings each comprise six peak portions and six valley portions, the valley portions of the first ring and the peak portions of the second ring being circumferentially offset from one another by approximately 30 degrees, the valley portions of the second ring and the peak portions of the third ring being circumferentially offset from one another by approximately 30 degrees.

17. The stent of claim 1 wherein the valley portions of the first ring and the peak portions of the second ring are circumferentially offset by about 0 to 10 degrees when the stent is in its first delivery, fully unexpanded position and the valley portions of the second ring and the peak portions of the third ring being circumferentially offset by about 0 to 10 degrees when the stent is in its first delivery, fully unexpanded position.

18. The stent of claim 1 wherein the width of the first struts, second struts, curved connectors, first intermediate struts and second intermediate struts is between about 0.0008 to 0.003 inches.

19. The stent of claim 1 wherein the major angle between the first and second struts is between about 35 to 55 degrees when the stent has been deployed into a vessel of recommended size.

20. The stent of claim 1 wherein the attachment angle between the first and second struts is between about 0 to 20 degrees.

21. The stent of claim 1 wherein one or more of the first and second struts, curved connectors and/or first and second intermediate struts comprise recesses for placement of a therapeutic agent or a radiopaque material.

22. The stent of claim 1 further comprising posts extending from one or more of the peak portions of the first ring.

23. The stent of claim 22 further comprising a radiopaque marker attached to the posts.

24. The stent of claim 1 wherein at least a portion of the stent is coated with a doped polymer containing a radiopaque material.

25. A stent comprising:
at least first, second, third and fourth spaced-apart, radially expandable rings that are substantially aligned along a longitudinal axis, each ring comprising a plurality of first struts and a plurality of second struts, the first and second struts being connected to form an undulating pattern that has peak portions and valley portions,
first curved connectors joining one or more of the valley portions of the first ring to one or more of the peak portions of the second ring, the valley portions and peak portions being circumferentially offset from one another,
second curved connectors joining one or more of the valley portions of the second ring to one or more of the peak portions of the third ring, the valley portions and peak portions being circumferentially offset from one another,
third curved connectors joining one or more of the valley portions of the third ring to one or more of the peak portions of the fourth ring, the valley portions and peak portions being circumferentially offset from one another,
a first intermediate strut extending between a first strut of the second ring to a first strut of the third ring without intersecting any of the other first and second struts and first and second curved connectors and;
a second intermediate strut extending between a second strut of the third ring to a second strut of the fourth ring without intersecting any of the other first and second struts and first and second curved connectors,
in use, the stent movable from a first delivery position to a second placement position, in the first delivery position the stent being in a fully unexpanded position and having a first diameter and in the second position the stent being in a radially expanded position and having a second diameter greater than the first diameter for placement at a treatment site of a patient;
wherein the first and second intermediate struts are connected to locations on the first and second struts, respectively, such that no portions of the first and second intermediate struts overlap either in a circumferential direction around the stent or in an axial direction along the stent when the stent is in the fully unexpanded position.

26. The stent of claim 25 wherein the width of the first and second struts of the first ring is greater than the width of the first and second struts of the second, third and fourth rings.

27. The stent of claim 25 wherein the thickness of the first and second struts of the first ring is greater than the thickness of the first and second struts of the second, third and fourth rings.

28. A stent comprising:
at least first, second and third spaced-apart, radially expandable rings that are substantially aligned along a longitudinal axis, each ring comprising a plurality of first struts and a plurality of second struts, the first and second struts being connected to form an undulating pattern that has peak portions and valley portions,
first curved connectors joining one or more of the valley portions of the first ring to one or more of the peak portions of the second ring, the valley portions and peak portions being circumferentially offset from one another,
second curved connectors joining one or more of the valley portions of the second ring to one or more of the peak portions of the third ring, the valley portions and peak portions being circumferentially offset from one another,
a first intermediate strut extending between a first strut of the first ring to a first strut of the second ring without intersecting any of the other first and second struts and first and second curved connectors and;
a second intermediate strut extending between a second strut of the second ring to a second strut of the third ring without intersecting any of the other first and second struts and first and second curved connectors,
in use, the stent movable from a first delivery position to a second placement position, in the first delivery position the stent being in a fully unexpanded position and having a first diameter and in the second position the stent being in a radially expanded position and having a second diameter greater than the first diameter for placement at a treatment site of a patient;
the first and second intermediate struts being connected to locations on the first and second struts, respectively, such that no portions of the first and second intermediate struts overlap either in a circumferential direction around the stent or in an axial direction along the stent when the stent is in the fully unexpanded position; and,
the stent being compressible to small diameters in its first delivery, fully unexpanded state to provide access to small diameter vessels.

29. A stent comprising:
at least first, second, third and fourth spaced-apart, radially expandable rings that are substantially aligned along a longitudinal axis, each ring comprising a plurality of first struts and a plurality of second struts, the first and second struts being connected to form an undulating pattern that has peak portions and valley portions,
first curved connectors joining one or more of the valley portions of the first ring to one or more of the peak portions of the second ring, the valley portions and peak portions being circumferentially offset from one another,
second curved connectors joining one or more of the valley portions of the second ring to one or more of the peak portions of the third ring, the valley portions and peak portions being circumferentially offset from one another,
third curved connectors joining one or more of the valley portions of the third ring to one or more of the peak portions of the fourth ring, the valley portions and peak portions being circumferentially offset from one another,
a first intermediate strut extending between a first strut of the second ring to a first strut of the third ring without intersecting any of the other first and second struts and first and second curved connectors and;
a second intermediate strut extending between a second strut of the third ring to a second strut of the fourth ring without intersecting any of the other first and second struts and first and second curved connectors,
in use, the stent movable from a first delivery position to a second placement position, in the first delivery position the stent being in a fully unexpanded position and having a first diameter and in the second position the stent being in a radially expanded position and having a second diameter greater than the first diameter for placement at a treatment site of a patient;

the first and second intermediate struts being connected to locations on the first and second struts, respectively, such that no portions of the first and second intermediate struts overlap either in a circumferential direction around the stent or in an axial direction along the stent when the stent is in the fully unexpanded position; and, the stent being compressible to small diameters in its first delivery, fully unexpanded state to provide access to small diameter vessels.

* * * * *